(12) United States Patent
Maschino et al.

(10) Patent No.: US 7,974,697 B2
(45) Date of Patent: Jul. 5, 2011

(54) MEDICAL IMAGING FEEDBACK FOR AN IMPLANTABLE MEDICAL DEVICE

(75) Inventors: Steven E. Maschino, Seabrook, TX (US); William R. Buras, Friendswood, TX (US)

(73) Assignee: Cyberonics, Inc., Houston, TX (US)

( * ) Notice: Subject to any disclaimer, the term of this patent is extended or adjusted under 35 U.S.C. 154(b) by 830 days.

(21) Appl. No.: 11/340,337

(22) Filed: Jan. 26, 2006

(65) Prior Publication Data
US 2007/0173902 A1    Jul. 26, 2007

(51) Int. Cl.
*A61N 1/36* (2006.01)
(52) U.S. Cl. .......................................................... 607/45
(58) Field of Classification Search ...................... 607/45
See application file for complete search history.

(56) References Cited

U.S. PATENT DOCUMENTS

| | | | |
|---|---|---|---|
| 4,702,254 A | 10/1987 | Zabara | |
| 4,867,164 A | 9/1989 | Zabara | |
| 5,025,807 A | 6/1991 | Zabara | |
| 5,081,987 A | 1/1992 | Nigam | |
| 5,154,172 A | 10/1992 | Terry, Jr. et al. | |
| 5,179,950 A | 1/1993 | Stanislaw | |
| 5,186,170 A | 2/1993 | Varrichio et al. | |
| 5,188,104 A | 2/1993 | Wernicke et al. | |
| 5,205,285 A | 4/1993 | Baker, Jr. | |
| 5,215,086 A | 6/1993 | Terry, Jr. et al. | |
| 5,217,010 A | 6/1993 | Tsitlik et al. | |
| 5,222,494 A | 6/1993 | Baker, Jr. | |
| 5,231,988 A | 8/1993 | Wernicke et al. | |
| 5,235,980 A | 8/1993 | Varrichio et al. | |
| 5,237,991 A | 8/1993 | Baker, Jr. et al. | |
| 5,263,480 A | 11/1993 | Wernicke et al. | |
| 5,269,303 A | 12/1993 | Wernicke et al. | |
| 5,299,569 A | 4/1994 | Wernicke et al. | |
| 5,304,206 A | 4/1994 | Baker, Jr. et al. | |
| 5,330,515 A | 7/1994 | Rutecki et al. | |
| 5,335,657 A | 8/1994 | Terry, Jr. et al. | |

(Continued)

FOREIGN PATENT DOCUMENTS
CA    2339971    6/2004
(Continued)

OTHER PUBLICATIONS

Henry Gray. "Anatomy of the Human Body." 1918, 1 page.*

*Primary Examiner* — Eric D. Bertram
(74) *Attorney, Agent, or Firm* — Chowdhurry Georgakis, P.C.; Jonathan D. Rowell; Darrell N. Fuller

(57) ABSTRACT

A method, system, and apparatus are provided for performing an adaptive stimulation process using medical imaging feedback data for affecting an operation of an implantable medical device. The first stimulation signal is applied to a neural structure for modulation of a target portion of the patient's brain associated with a disorder. Medical imaging data is acquired that is indicative of whether the target portion of the brain is modulated as a result of the first stimulation signal. The first signal characteristic is modified to generate a second stimulation signal in response to a determination that said target portion of the brain is not modulated as a result of said first stimulation signal. The first and second stimulation signals may be used to navigate an effect of the first and second stimulation signals until a targeted portion of the human body is stimulated according to a predetermined threshold.

10 Claims, 11 Drawing Sheets

U.S. PATENT DOCUMENTS

| | | |
|---|---|---|
| 5,434,611 A | 7/1995 | Tamura |
| 5,441,047 A | 8/1995 | David et al. |
| 5,518,001 A | 5/1996 | Snell |
| 5,522,862 A | 6/1996 | Testerman et al. |
| 5,531,778 A | 7/1996 | Maschino et al. |
| 5,540,730 A | 7/1996 | Terry, Jr. et al. |
| 5,540,734 A | 7/1996 | Zabara |
| 5,544,649 A | 8/1996 | David et al. |
| 5,553,609 A | 9/1996 | Chen et al. |
| 5,569,186 A | 10/1996 | Lord et al. |
| 5,571,150 A | 11/1996 | Wernicke et al. |
| 5,690,681 A | 11/1997 | Geddes et al. |
| 5,700,282 A | 12/1997 | Zabara |
| 5,702,429 A | 12/1997 | King |
| 5,707,400 A | 1/1998 | Terry, Jr. et al. |
| 5,743,860 A | 4/1998 | Hively et al. |
| 5,814,092 A | 9/1998 | King |
| 5,913,882 A | 6/1999 | King |
| 5,916,239 A | 6/1999 | Geddes et al. |
| 5,928,272 A | 7/1999 | Adkins et al. |
| 5,995,868 A | 11/1999 | Osorio et al. |
| 6,018,682 A | 1/2000 | Rise |
| 6,104,956 A | 8/2000 | Naritoku et al. |
| 6,112,116 A | 8/2000 | Fischell et al. |
| 6,141,590 A | 10/2000 | Renirie et al. |
| 6,198,958 B1 | 3/2001 | Ives et al. |
| 6,205,359 B1 | 3/2001 | Boveja |
| 6,208,902 B1 | 3/2001 | Boveja |
| 6,221,908 B1 | 4/2001 | Kilgard et al. |
| 6,253,109 B1 | 6/2001 | Gielen |
| 6,269,270 B1 | 7/2001 | Boveja |
| 6,304,775 B1 | 10/2001 | Iasemidis et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,788 B2 | 3/2002 | Boveja |
| 6,366,813 B1 | 4/2002 | DiLorenzo |
| 6,366,814 B1 | 4/2002 | Boveja et al. |
| 6,425,852 B1 | 7/2002 | Epstein et al. |
| 6,449,507 B1 | 9/2002 | Hill et al. |
| 6,449,512 B1 | 9/2002 | Boveja |
| 6,463,328 B1 | 10/2002 | John |
| 6,473,639 B1 | 10/2002 | Fischell et al. |
| 6,473,644 B1 | 10/2002 | Terry, Jr. et al. |
| 6,473,652 B1 | 10/2002 | Sarwal et al. |
| 6,480,743 B1 | 11/2002 | Kirkpatrick et al. |
| 6,484,132 B1 | 11/2002 | Hively et al. |
| 6,487,446 B1 | 11/2002 | Hill et al. |
| 6,505,074 B2 | 1/2003 | Boveja et al. |
| 6,532,388 B1 | 3/2003 | Hill et al. |
| 6,549,804 B1 | 4/2003 | Osorio et al. |
| 6,560,486 B1 | 5/2003 | Osorio et al. |
| 6,564,102 B1 | 5/2003 | Boveja |
| 6,587,719 B1 | 7/2003 | Barrett et al. |
| 6,587,726 B2 | 7/2003 | Lurie et al. |
| 6,587,727 B2 | 7/2003 | Osorio et al. |
| 6,594,524 B2 | 7/2003 | Esteller et al. |
| 6,600,956 B2 | 7/2003 | Maschino et al. |
| 6,609,025 B2 | 8/2003 | Barrett et al. |
| 6,610,713 B2 | 8/2003 | Tracey |
| 6,611,715 B1 | 8/2003 | Boveja |
| 6,612,983 B1 | 9/2003 | Marchal |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,668,191 B1 | 12/2003 | Boveja |
| 6,671,555 B2 | 12/2003 | Gielen et al. |
| 6,671,556 B2 | 12/2003 | Osorio et al. |
| 6,711,440 B2 | 3/2004 | Deal et al. |
| 6,718,203 B2 | 4/2004 | Weiner et al. |
| 6,718,207 B2 | 4/2004 | Connelly |
| 6,721,603 B2 | 4/2004 | Zabara et al. |
| 6,757,566 B2 | 6/2004 | Weiner et al. |
| 6,760,626 B1 | 7/2004 | Boveja |
| 6,768,969 B1 | 7/2004 | Nikitin et al. |
| 6,778,856 B2 | 8/2004 | Connelly et al. |
| 6,785,568 B2 | 8/2004 | Chance |
| 6,793,670 B2 | 9/2004 | Osorio et al. |
| 6,795,730 B2 | 9/2004 | Connelly et al. |
| 6,795,736 B2 | 9/2004 | Connelly et al. |
| 6,799,069 B2 | 9/2004 | Weiner et al. |
| 6,804,656 B1 | 10/2004 | Rosenfeld et al. |
| 6,819,954 B2 | 11/2004 | Connelly |
| 6,819,956 B2 | 11/2004 | DiLorenzo |
| 6,845,266 B2 | 1/2005 | Weiner et al. |
| 6,904,390 B2 | 6/2005 | Nikitin et al. |
| 6,920,357 B2 | 7/2005 | Osorio et al. |
| 6,934,580 B1 | 8/2005 | Osorio et al. |
| 6,944,501 B1 | 9/2005 | Pless |
| 6,949,929 B2 | 9/2005 | Gray et al. |
| 6,954,674 B2 | 10/2005 | Connelly |
| 6,961,618 B2 | 11/2005 | Osorio et al. |
| 7,006,859 B1 | 2/2006 | Osorio et al. |
| 7,006,872 B2 | 2/2006 | Gielen et al. |
| 2002/0072782 A1 | 6/2002 | Osorio et al. |
| 2002/0099417 A1 | 7/2002 | Naritoku et al. |
| 2002/0188214 A1 | 12/2002 | Misczynski et al. |
| 2003/0036781 A1* | 2/2003 | Nuttin et al. .................. 607/45 |
| 2003/0074032 A1 | 4/2003 | Gliner |
| 2003/0083716 A1 | 5/2003 | Nicolelis et al. |
| 2003/0088274 A1 | 5/2003 | Gliner et al. |
| 2003/0097161 A1 | 5/2003 | Firlik et al. |
| 2003/0125786 A1 | 7/2003 | Gliner et al. |
| 2003/0130706 A1 | 7/2003 | Sheffield et al. |
| 2003/0212440 A1 | 11/2003 | Boveja |
| 2004/0088024 A1 | 5/2004 | Firlik et al. |
| 2004/0122484 A1 | 6/2004 | Hatlestad et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138647 A1 | 7/2004 | Osorio et al. |
| 2004/0138711 A1 | 7/2004 | Osorio et al. |
| 2004/0138721 A1* | 7/2004 | Osorio et al. .................. 607/45 |
| 2004/0158119 A1 | 8/2004 | Osorio et al. |
| 2004/0172094 A1 | 9/2004 | Cohen et al. |
| 2004/0176831 A1 | 9/2004 | Gliner et al. |
| 2004/0260346 A1 | 12/2004 | Overall et al. |
| 2004/0263172 A1 | 12/2004 | Gray et al. |
| 2005/0004621 A1 | 1/2005 | Boveja et al. |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0033378 A1 | 2/2005 | Sheffield et al. |
| 2005/0038326 A1 | 2/2005 | Mathur |
| 2005/0049515 A1 | 3/2005 | Misczynski et al. |
| 2005/0049655 A1 | 3/2005 | Boveja et al. |
| 2005/0070971 A1 | 3/2005 | Fowler et al. |
| 2005/0075679 A1 | 4/2005 | Gliner et al. |
| 2005/0075680 A1 | 4/2005 | Lowry et al. |
| 2005/0101873 A1 | 5/2005 | Misczynski et al. |
| 2005/0119703 A1 | 6/2005 | DiLorenzo |
| 2005/0124901 A1 | 6/2005 | Misczynski et al. |
| 2005/0131467 A1 | 6/2005 | Boveja et al. |
| 2005/0131486 A1 | 6/2005 | Boveja et al. |
| 2005/0131493 A1 | 6/2005 | Boveja et al. |
| 2005/0143786 A1 | 6/2005 | Boveja et al. |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0187590 A1 | 8/2005 | Boveja et al. |
| 2005/0187796 A1 | 8/2005 | Rosenfeld et al. |
| 2005/0192644 A1 | 9/2005 | Boveja et al. |
| 2005/0197590 A1 | 9/2005 | Osorio et al. |
| 2005/0222642 A1 | 10/2005 | Przybyszewski et al. |

FOREIGN PATENT DOCUMENTS

| | | |
|---|---|---|
| EP | 0944411 | 4/2001 |
| EP | 1145736 | 10/2001 |

| | | | | | | |
|---|---|---|---|---|---|---|
| WO | 9302744 | 2/1993 | | WO | 2007124126 | 11/2007 |
| WO | 2004036377 | 4/2004 | | WO | 2007124190 | 11/2007 |
| WO | 2005007120 | 1/2005 | | WO | 2007124192 | 11/2007 |
| WO | 2005007232 | 1/2005 | | | | |
| WO | 2005067599 | 7/2005 | | | | |

* cited by examiner

MEDICAL IMAGING FEEDBACK FOR AN IMPLANTABLE MEDICAL DEVICE

BACKGROUND OF THE INVENTION

1. Field of the Invention

This invention relates generally to implantable medical devices, and, more particularly, to methods, apparatus, and systems for using feedback data from a medical imaging system to affect an operation performed by an implantable medical device (IMD).

2. Description of the Related Art

There have been many improvements over the last several decades in medical treatments for disorders of the nervous system, such as epilepsy and other motor disorders, and abnormal neural discharge disorders. One of the more recently available treatments involves the application of an electrical signal to reduce various symptoms or effects caused by such neural disorders. For example, electrical signals have been successfully applied at strategic locations in the human body to provide various benefits, including reducing occurrences of seizures and/or improving or ameliorating other conditions. Examples of such a treatment regimen involve applying an electrical signal to the vagus nerve of the human body to reduce or eliminate epileptic seizures, as described in U.S. Pat. Nos. 4,702,254, 4,867,164, and 5,025,807 to Dr. Jacob Zabara, and the treatment of neuropsychiatric disorders such as depression, as described in U.S. Pat. No. 5,299,569 to Joachim Wernicke et al. The foregoing patents are hereby incorporated in their entirety herein by reference in this specification. Electrical stimulation of cranial nerves, such as the vagus nerve (hereinafter referred to as vagus nerve stimulation therapy or VNS) may be provided by implanting an electrical device underneath the skin of a patient and performing a detection and electrical stimulation process. This type of stimulation is generally referred to as "active," "feedback," or "triggered" stimulation. Alternatively, the system may operate without a detection system once the patient has been diagnosed with a disorder treatable by cranial nerve stimulation (such as epilepsy or depression), and may periodically apply a series of electrical pulses to the cranial nerve intermittently throughout the day, or over another predetermined time interval. This type of stimulation is generally referred to as "passive," "non-feedback," or "prophylactic," stimulation. An implantable medical device that is implanted within the patient's body may apply the stimulation.

State-of-the-art implantable medical devices generally deliver stimulation signals to one or more regions of a patient's body in a predetermined periodic cycle. Based upon the diagnosed disorder of the patient, a physician may determine a regimen of therapeutic stimulation signals to treat the disorder. The devices then execute the predetermined therapy regimen. This regimen may be interrupted by predetermined interruption protocols, such as an external communication from a physician prompting a change in the regimen, a signal from the patient, etc.

As used herein, "stimulation" refers to the application of an electrical, mechanical, and/or chemical signal to a neural structure in the patient's body. In one embodiment, the stimulation comprises an electrical signal. The stimulation signal may induce afferent and/or efferent action potentials on the nerve, may block native afferent and/or efferent action potentials, or may be applied at a sub-threshold level that neither generates action potentials nor blocks native action potentials. In some embodiments, the stimulation signal is a signal that is capable of inducing afferent and/or efferent action potentials on the nerve.

The stimulation signal applied to the neural structure in embodiments of the present invention refers to an exogenous signal that is distinct from the endogenous electrical, mechanical, and chemical activity (e.g., afferent and/or efferent electrical action potentials) generated by the patient's body and environment. In other words, the stimulation signal (whether electrical, mechanical or chemical in nature) applied to the nerve in the present invention is a signal applied from an artificial source, e.g., a neurostimulator.

Providing an electrical signal for stimulation of a cranial nerve may cause variations in the electrical activity of portions of a patient's brain. However, state-of-the-art IMDs generally do not allow for affecting the predetermined stimulation regimens in response to these physiological brain variations. Barring active initiation of operational changes prompted by an external source, such as a physician, state-of-the-art implantable medical devices generally continue a predetermined treatment regimen despite the physiological variations in the brain. This may cause the implantable medical device to become less accurate in targeting specific regions of the brain for treating specific disorders. Further, state-of-the-art medical systems generally do not have sufficient feedback as to the effectiveness of the stimulation in terms of targeting certain regions of the brain.

Generally, state-of-the-art electrical IMDs may cause a reaction in a patient's brain by stimulation of cranial nerves. The effects of the stimulation are evaluated on a long-term basis, where physicians may evaluate whether sufficient improvement relating to the disorder has taken place over time. However, this methodology generally lacks the ability to perform more short-term adjustments. In other words, the time period between delivering stimulation and studying the effects of the stimulation is substantially long—typically months or even exceeding a year. Therefore, a substantial amount of time may elapse to determine whether a stimulation regimen has improved the treatment or condition. Thus, finding the appropriate stimulation regimen can be delayed substantially due to the state-of-the-art methodologies.

In an attempt to alleviate some of these problems, designers have provided for altering the regimen based on an external input or input from the patient, for example, through a magnetic signal sent to the implantable medical device. However, this solution may not be sufficiently reactive to adequately address variations in the brain resulting from particular stimulation regimens. For example, a patient is generally unable to determine the effects of the stimulation to certain portions of the brain. Further, these solutions may require an assessment by an external source, such as a physician or the patient. By the time an external source examines the physiological variations produced by the stimulation, the patient's brain may have undergone further changes, rendering any reaction to the original physiological variations obsolete.

Even though delivery of stimulation signals may cause specific physiological variations in the patient's brain, state-of-the-art implantable medical devices generally behave independently of such variations, at least in the short term. Long-term changes may be provided by re-examination by a physician, i.e. re-diagnosis of a disorder, and then making further adjustments to the stimulation treatment. This may result in significant delay between the physiological changes that may occur due to stimulation, and the time when a physician makes manual adjustments to the stimulation regimen after examination. Therefore, efficient and effective reaction to physiological changes may not take place utilizing state-of-the-art implantable medical devices. Further, targeted regions of the brain may not be adequately affected by a particular stimulation regime, possibly leading to reduced treatment efficacy.

The present invention is directed to overcoming, or at least reducing, the effects of one or more of the problems set forth above.

SUMMARY OF THE INVENTION

In one aspect, the present invention comprises a method for providing an adaptive stimulation using an implantable medical device. A first stimulation signal based upon a first signal characteristic is provided using the IMD. The first stimulation signal is applied to a neural structure for modulation of a target portion of the patient's brain associated with a disorder. The method further includes acquiring, using a medical imaging system, medical imaging data that is indicative of whether the target portion of the brain is modulated as a result of the first stimulation signal. The medical imaging system may be a computed axial tomography (CAT) device, a phototron emission tomography (PET) device, a single photon emission computed tomography (SPECT) device, an electroencephalography (EEG) device, a magneto encephalography (MEG) device, a diffuse optical tomography device (DOT), an ultrasound device, an X-ray device, a functional transcranial doppler device, or a magnetic resonance spectroscopy (MRS) device. The first signal characteristic is modified to generate a second stimulation signal in response to a determination that the target portion of the brain is not modulated as a result of the first stimulation signal. In one embodiment, the first stimulation signal is an electrical signal.

In another aspect, the present invention comprises a method for providing an adaptive stimulation using medical imaging data for affecting an operation of an IMD. A first stimulation signal having a first signal characteristic is provided to treat a disorder. The first stimulation signal is applied to a neural structure to provide an effect on a predetermined region of the brain associated with the disorder. The method also comprises using a medical imaging device to acquire medical imaging data responsive to the first stimulation signal. A determination is made based upon the medical imaging data whether the first stimulation signal has sufficiently affected the predetermined region of the brain. The method further comprises modifying the first characteristic of the first stimulation signal to generate a second stimulation signal based upon a determination that the predetermined region of the brain has not been sufficiently affected by the first stimulation signal. Finally, the method includes navigating an effect of the second stimulation signal to the predetermined region of the brain. Navigating the effect of the second stimulation signal includes iteratively guiding stimulation effects relating to said first and second stimulation signals throughout a plurality of regions of the brain to modulate a targeted region of the brain.

In one aspect, the present invention comprises a method for providing an adaptive stimulation process using medical imaging feedback data for affecting an operation of an IMD. A target portion of the brain is correlated to a disorder. A first brain map is generated comprising data relating to the state of the brain during a time period prior to applying a first stimulation signal to a neural structure of the brain. A first stimulation signal having a first characteristic is provided to treat the disorder, and the signal is applied to the neural structure of the patient. A second brain map is generated comprising data relating to the state of the brain during at least one of a time period at least partially during the step of applying the first stimulation signal and a time period after applying the first stimulation signal. The first brain map is compared to the second brain map to compute a brain-map difference, and a third brain map is generated comprising data relating to the brain-map difference. The third brain map includes data indicative of whether the target portion of the brain has been modulated by the first stimulation signal. The first signal characteristic is modified to generate a second stimulation signal based upon a determination that the target portion of the brain was not modulated by the first stimulation signal.

In one aspect, the present invention comprises an implantable medical system for treating a physiological disorder. The implantable medical system comprises: an implantable medical device (IMD) for providing a first stimulation signal comprising a first signal characteristic to a portion of a cranial nerve to treat a disorder. The system also includes an electrode, operatively coupled to the IMD, to apply the first stimulation signal from the IMD to the portion of the patient's body. The system also includes a medical imaging system operatively coupled to the IMD. The medical imaging system is adapted to acquire medical imaging data responsive to the first stimulation signal and indicative of whether a target portion of the brain corresponding to the disorder is substantially modulated as a result of the first stimulation signal. The medical imaging system may comprise a computed axial tomography (CAT) device, a phototron emission tomography (PET) device, a single photon emission computed tomography (SPECT) device, an electroencephalography (EEG) device, a magneto encephalography (MEG) device, a diffuse optical tomography device (DOT), a functional transcranial doppler device, an ultrasound device, an X-ray device, or a magnetic resonance spectroscopy (MRS) device. The IMD comprises a stimulation feedback unit for modifying the first signal characteristic based upon a determination that the target portion of the brain is not substantially modulated as a result of the first stimulation to generate a second stimulation signal.

BRIEF DESCRIPTION OF THE DRAWINGS

The invention may be understood by reference to the following description taken in conjunction with the accompanying drawings, in which like reference numerals identify like elements, and in which.

Figure 1A:
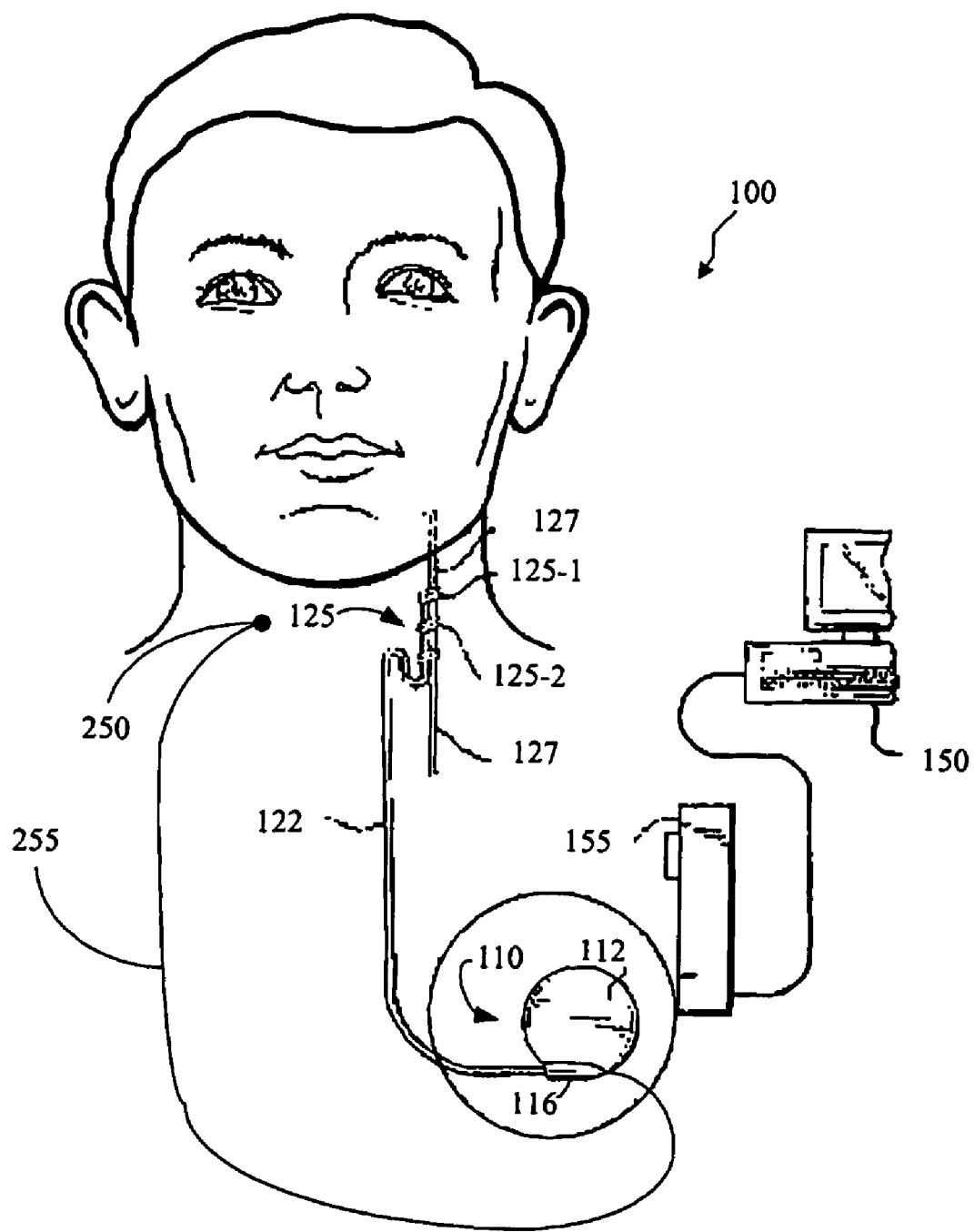
FIGS. 1A-1D provide stylized diagrams of an implantable medical device implanted into a patient's body for providing stimulation to a portion of the patient's body, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Embodiments of the present invention provide for an adaptive therapeutic stimulation using an implantable medical device. Embodiments of the present invention provide for using an implantable medical device for delivering a therapeutic stimulation based upon imaging data relating to a region of the brain. The imaging data may be resultant data from a brain scan. The brain scan/imaging data may be acquired by a medical imaging system that is strategically timed with the operation of the implantable medical device. The brain scan data may include indications of a chemical, electrical, and/or biological variation in a brain region resulting from the stimulation. Based upon the imaging data, at least one stimulation parameter may be adaptively modified for subsequent stimulations.

Although not so limited, a system capable of implementing embodiments of the present invention is described below. FIGS. 1A-1D depict a stylized implantable medical system 100 for implementing one or more embodiments of the present invention. FIGS. 1A-1D illustrate an electrical signal generator 110 having main body 112 comprising a case or shell 121 (FIG. 1A) with a header 116 (FIG. 1C) for connecting to leads 122. The generator 110 is implanted in the patient's chest in a pocket or cavity formed by the implanting surgeon just below the skin (indicated by a dotted line 145, FIG. 1B), similar to the implantation procedure for a pacemaker pulse generator.

Figure 1B:
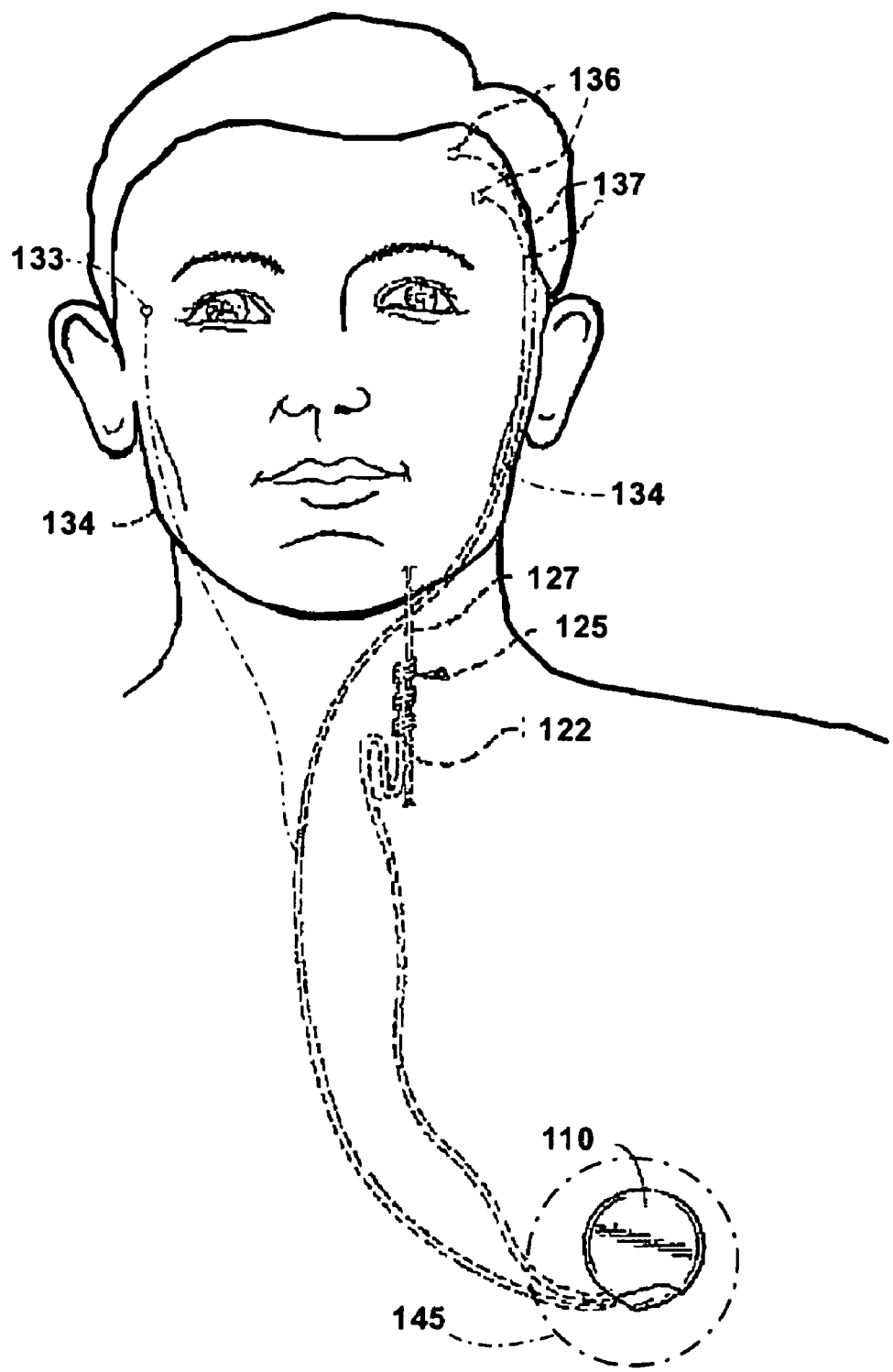
Figure 1C:
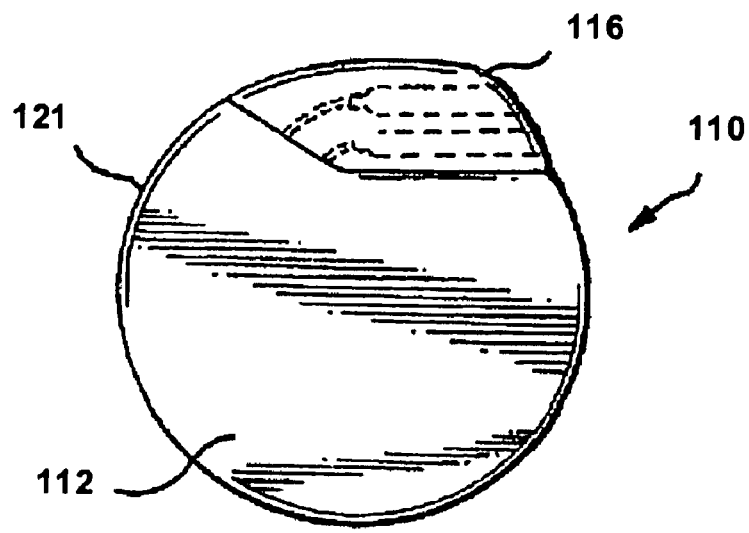
Figure 1D:
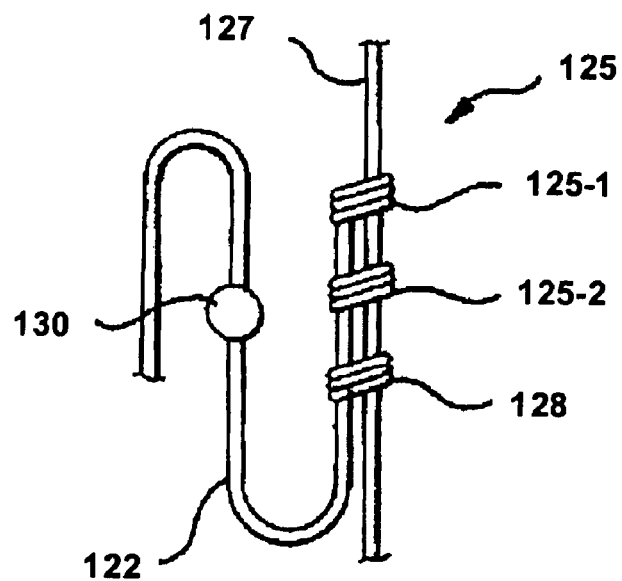

A stimulating nerve electrode assembly 125, preferably comprising an electrode pair, is conductively connected to the distal end of an insulated, electrically conductive lead assembly 122, which preferably comprises a pair of lead wires (one wire for each electrode of an electrode pair). Lead assembly 122 is attached at its proximal end to connectors on the header 116 (FIG. 1C) on case 121. The electrode assembly 125 may be surgically coupled to a vagus nerve 127 in the patient's neck or at another location, e.g., near the patient's diaphragm. Other cranial nerves may also be used to deliver the electrical neurostimulation signal. The electrode assembly 125 preferably comprises a bipolar stimulating electrode pair 125-1, 125-2 (FIG. 1D), such as the electrode pair described in U.S. Pat. No. 4,573,481 issued Mar. 4, 1986 to Bullara. Suitable electrode assemblies are available from Cyberonics, Inc., Houston, Tex., USA as the Model 302 electrode assembly. However, persons of skill in the art will appreciate that many electrode designs could be used in the present invention. The two electrodes are preferably wrapped about the vagus nerve, and the electrode assembly 125 may be secured to the nerve 127 by a spiral anchoring tether 128 (FIG. 1D) such as that disclosed in U.S. Pat. No. 4,979,511 issued Dec. 25, 1990 to Reese S. Terry, Jr. and assigned to the same assignee as the instant application. Lead assembly 122 is secured, while retaining the ability to flex with movement of the chest and neck, by a suture connection 130 to nearby tissue (FIG. 1D).

In one embodiment, the open helical design of the electrode assembly 125 (described in detail in the above-cited Bullara patent), which is self-sizing and flexible, minimizes mechanical trauma to the nerve and allows body fluid interchange with the nerve. The electrode assembly 125 preferably conforms to the shape of the nerve, providing a low stimulation threshold by allowing a large stimulation contact area with the nerve. Structurally, the electrode assembly 125 comprises two electrode ribbons (not shown), of a conductive material such as platinum, iridium, platinum-iridium alloys, and/or oxides of the foregoing. The electrode ribbons are individually bonded to an inside surface of an elastomeric body portion of the two spiral electrodes 125-1 and 125-2 (FIG. 1D), which may comprise two spiral loops of a three-loop helical assembly. The lead assembly 122 may comprise two distinct lead wires or a coaxial cable whose two conductive elements are respectively coupled to one of the conductive electrode ribbons. One suitable method of coupling the lead wires or cable to the electrodes 125-1, 125-2 comprises a spacer assembly such as that disclosed in U.S. Pat. No. 5,531,778, although other known coupling techniques may be used.

The elastomeric body portion of each loop is preferably composed of silicone rubber, and the third loop 128 (which typically has no electrode) acts as the anchoring tether for the electrode assembly 125.

In certain embodiments of the invention, sensors such as eye movement sensing electrodes 133 (FIG. 1B) may be implanted at or near an outer periphery of each eye socket in a suitable location to sense muscle movement or actual eye movement. The electrodes 133 may be electrically connected to leads 134 implanted via a catheter or other suitable means (not shown) and extending along the jaw line through the neck and chest tissue to the header 116 of the electrical pulse generator 110. When included in systems of the present invention, the sensing electrodes 133 may be utilized for detecting rapid eye movement (REM) in a pattern indicative of a disorder to be treated, as described in greater detail below. The detected indication of the disorder can be used to trigger active stimulation.

Other sensor arrangements may alternatively or additionally be employed to trigger active stimulation. Referring again to FIG. 1B, electroencephalograph (EEG) sensing electrodes 136 may optionally be implanted and placed in spaced-apart relation on the skull, and connected to leads 137 implanted and extending along the scalp and temple, and then connected to the electrical pulse generator 110 along the same path and in the same manner as described above for the eye movement electrode leads 134.

In alternative embodiments, temperature sensing elements and/or heart rate sensor elements may be employed to trigger active stimulation. In addition to active stimulation incorporating sensor elements, other embodiments of the present invention utilize passive stimulation to deliver a continuous, periodic or intermittent electrical signal (each of which constitutes a form of continual application of the signal) to the vagus nerve according to a programmed on/off duty cycle without the use of sensors to trigger therapy delivery. Both passive and active stimulation may be combined or delivered by a single IMD according to the present invention. Either or both modes may be appropriate to treat the particular disorder diagnosed in the case of a specific patient under observation.

The electrical pulse generator 110 may be programmed with an external computer 150 using programming software of the type copyrighted by the assignee of the instant application with the Register of Copyrights, Library of Congress, or other suitable software based on the description herein, and a programming wand 155 to facilitate radio frequency (RF) communication between the computer 150 (FIG. 1A) and the pulse generator 110. The wand 155 and software permit non-invasive communication with the generator 110 after the latter is implanted. The wand 155 is preferably powered by internal batteries, and provided with a "power on" light to indicate sufficient power for communication. Another indicator light may be provided to show that data transmission is occurring between the wand and the generator.

A variety of stimulation therapies may be provided in implantable medical systems 100 of the present invention. Different types of nerve fibers (e.g., A, B, and C fibers being different fibers targeted for stimulation) respond differently to stimulation from electrical signals. More specifically, the different types of nerve fibers have different conduction velocities and stimulation thresholds and, therefore, differ in their responsiveness to stimulation. Certain pulses of an electrical stimulation signal, for example, may be below the stimulation threshold for a particular fiber and, therefore, may generate no action potential in the fiber. Thus, smaller or narrower pulses may be used to avoid stimulation of certain nerve fibers (such as C fibers) and target other nerve fibers (such as A and/or B fibers, which generally have lower stimulation thresholds and higher conduction velocities than C fibers). Additionally, techniques such as pre-polarization may be employed wherein particular nerve regions may be polarized before a more robust stimulation is delivered, which may better accommodate particular electrode materials. Furthermore, opposing polarity phases separated by a zero current phase may be used to excite particular axons or postpone nerve fatigue during long-term stimulation.

As used herein, the terms "stimulating" and "stimulator" may generally refer to delivery of a signal, stimulus, or impulse to neural tissue for affecting neuronal activity of a neural tissue (e.g., a volume of neural tissue in the brain or a nerve). The effect of such stimulation on neuronal activity is termed "modulation"; however, for simplicity, the terms "stimulating" and "modulating", and variants thereof, are sometimes used interchangeably herein. In general, however, the delivery of an exogenous signal refers to "stimulation" of the neural structure, while the effects of that signal, if any, on the neural structure are properly referred to as "modulation." The effect of delivery of the stimulation signal to the neural tissue may be excitatory or inhibitory and may potentiate acute and/or long-term changes in neuronal activity. For example, the "modulating" effect of the stimulation signal to the neural tissue may comprise one more of the following effects: (a) changes in neural tissue to initiate an action potential (bi-directional or uni-directional); (b) inhibition of conduction of action potentials (endogenous or externally stimulated) or blocking the conduction of action potentials (hyperpolarizing or collision blocking), (c) affecting changes in neurotransmitter/neuromodular release or uptake, and (d) changes in neuro-plasticity or neurogenesis of brain tissue.

In one embodiment, treatment of neuropsychiatric mood disorders is proposed. Mood disorders for which treatment is contemplated include, but are not limited to, depression, major depressive disorder, bipolar disorder, dysthymic disorder, and anxiety disorders. Anxiety disorders include, but are not limited to, obsessive compulsive disorder (OCD), post-traumatic stress syndrome (PTSD), panic disorder, generalized anxiety, simple phobia and social phobia. For ease of reference, the use of the term "mood disorder" herein also includes the above-named disorders.

In another embodiment, treatment of eating disorders is contemplated to include, but is not limited to, bulimia nervosa, anorexia nervosa, compulsive and binge eating, and obesity. Several familiar types of eating disorders are bulimia nervosa and anorexia nervosa. Bulimia nervosa ("bulimia") is an eating disorder in which an individual experiences recurrent episodes of insatiable craving for food often resulting in episodes of binge eating followed by inappropriate compensatory behavior to prevent weight gain. The inappropriate compensatory behavior typically includes self-induced vomiting, fasting, excessive exercise, and use of laxatives and diuretics. People suffering from bulimia commonly engage in binge eating and inappropriate compensatory behavior an average of two times a week for a period of three or more months. Treatments to address these disorders include physiological treatments, as well as psychological and psychiatric treatments. Besides drug regimens, invasive medical procedures, and/or counseling, effective treatment of such diseases and disorders are somewhat limited. Further, certain patients may not react favorably to various types of drugs or other treatments.

Yet another embodiment includes treatment of a disorder of the endocrine stress system. This includes disorders associated with the hypothalmus-pituitary-adrenal (HPA) axis and sympathetic-adrenal medullary (SAM) axis and includes, but is not limited to, disorders of the hormone system and energy metabolism-related disorders.

Embodiments of the present invention provide for a method, apparatus, and a system for performing a medical imaging analysis for providing an adaptive stimulation using an implantable medical device (IMD). A medical imaging device may be used to detect physiological variations and/or a physiological condition in a target portion of a patient's brain. The target portion of the brain may relate to a region of the brain that is correlated to a particular disorder that is being treated. The physiological variations in the brain regions may be used to adaptively adjust the therapy stimulation provided by the IMD 200. Additionally, physiological variations in the brain regions may be used to adaptively adjust one or more stimulation parameter(s). In some embodiments, the IMD may be partially implantable and may include an implantable stimulating electrode coupled, via a wireless link or through a secondary coil, to an external (i.e., outside the patient's body) pulse generator unit having a primary coil.

A medical imaging technique may be used to examine the effects of a stimulation provided to a portion of a patient's body, such as a cranial nerve. Data relating to the medical imaging may be analyzed and correlated to a particular stimulation and/or to particular disorders being treated. Based upon this correlation, an adaptive adjustment(s) to the stimulation may then be performed. A predetermined correlation of various regions of the brain and the particular disorder being treated may be used to determine if a stimulation signal is adequately affecting a targeted region of the brain. As a result of this analysis, a multi-focal stimulation may be performed in an adaptive manner such that a path to the targeted region of the brain may be followed until the targeted region has been adequately stimulated. Such a "safe cracking" technique may be used to "unlock" various neural pathways using feedback from medical imaging and correlating the feedback data to a stimulation. In this way, a pathway to a targeted region of the brain may be found in an adaptive manner. Utilizing embodiments of the present invention, a more efficient method of adjusting stimulation parameter to target a region of the brain to treat a particular disorder is made possible. Using this analysis, a more accurate treatment regimen for delivering therapy stimulation by the IMD 200 may be adjusted.

Further, in addition or alternative to modifying existing stimulation parameter(s), a second portion of the patient's body (e.g., a cranial nerve) may be stimulated based upon the analysis described above. This provides for a sequential and/or an overlapping stimulation process to determine whether a target region of the brains is being stimulated. This feedback and sequential and/or overlapping stimulation may be used to navigate through the cranial nerves or the brain stem, to various targeted portions of the brain.

Figure 2:
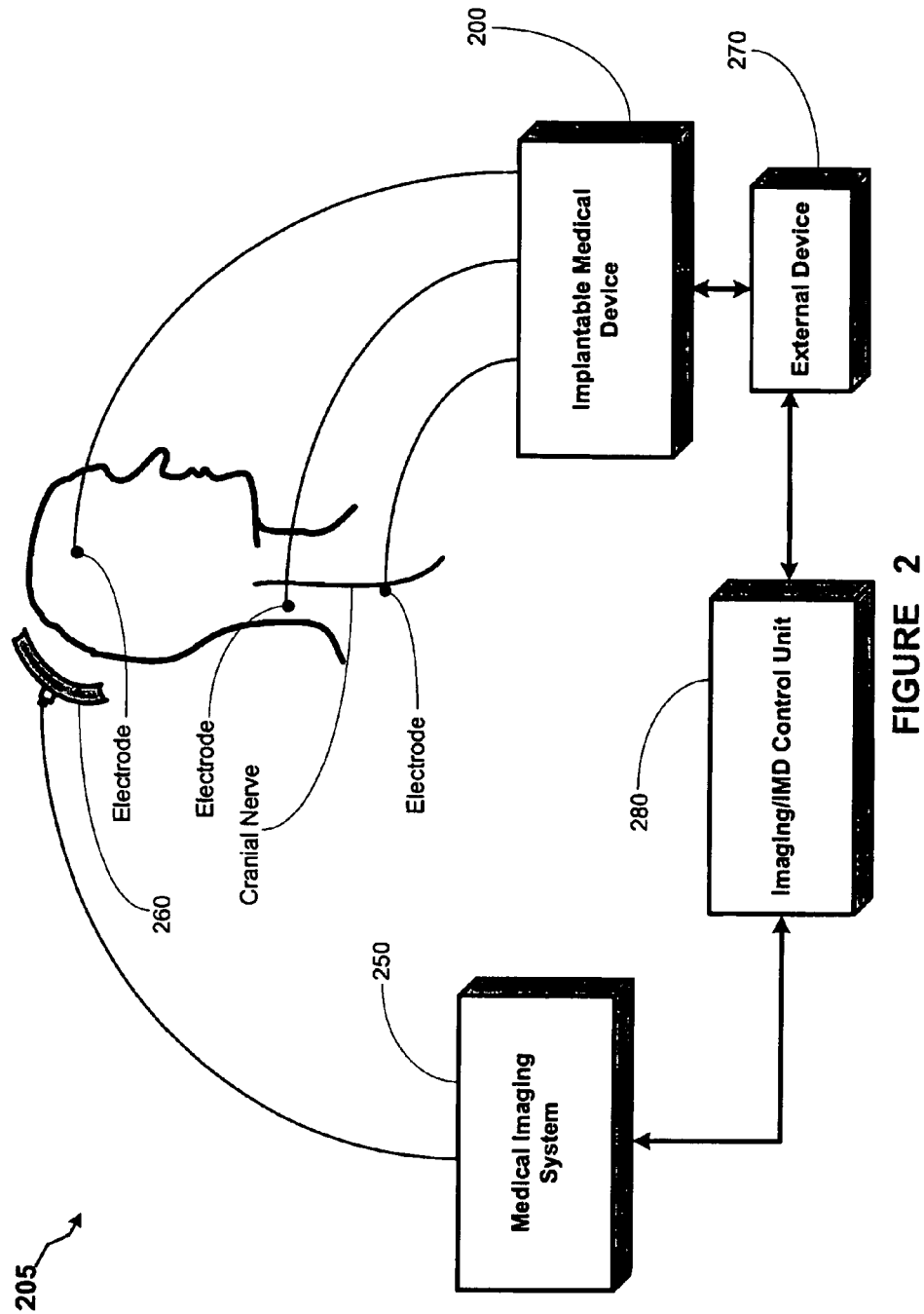
FIG. 2 illustrates a therapeutic stimulation system that includes an implantable medical device for delivering a therapy and a medical imaging system to examine the effects of therapy, in accordance with an illustrative embodiment of the present invention.

Turning now to FIG. 2, a stylized depiction of an implantable medical device system 205 and a medical imaging system being applied to a patient, in accordance with one illustrative embodiment of the present invention, is provided. FIG. 2 illustrates an IMD 200 that is capable of delivering stimulation signals to a portion of the patient's body, such as to a cranial nerve, and/or to a portion of the brain. For example, a stimulation signal may be delivered to a cranial nerve, such as the vagus nerve. In the generally accepted clinical labeling of cranial nerves, the tenth cranial nerve is the vagus nerve, which originates from brainstem. The vagus nerve passes through the foramina of the skull to parts of the head, neck and trunk. The vagus nerve branches into left and right branches, or vagi, upon exiting the skull. Left and right vagus nerve branches include both sensory and motor nerve fibers. One or more other cranial nerves may be stimulated in addition to the vagus nerve, including the trigeminal nerve (cranial nerve V), the vestibulocochlear nerve (cranial nerve VIII), and the glossopharyngeal nerve (cranial nerve IX), among others. The term "cranial nerve" refers to any portion of the main trunk or any branch of the cranial nerve including cranial nerve fibers, a left cranial nerve, and a right cranial nerve.

FIG. 2 also illustrates that the IMD 200 may provide stimulation to a region of the brain and/or the brain stem. Control signals that affect the operation of the IMD 200 may be provided by an external device 270, which may send data and receive data to and from the IMD 200. In response to performing stimulation, the medical imaging system 250 may acquire medical imaging data relating to the brain. A scanning device 260 may acquire medical imaging data from the cranial region of the patient. An imaging/IMD control unit 280 may control the synchronization of stimulation and the acquisition of subsequent medical imaging data to provide feedback data from the medical imaging system 250 to the external device 270 and on to the IMD 200. The imaging/IMD control unit 280 provides for facilitating a control feedback loop such that the IMD 200 may perform an adaptive control of the stimulation that is delivered to the patient. Further description of the various portions of the system illustrated in FIG. 2, is provided below.

In one embodiment, the IMD 200 is programmed to a set of parameters to deliver a range of stimuli to the cranial nerve to initially activate the areas of the brainstem, medulla, and the pons, which contain the initial synaptic pathways projecting from the vagus nerve axons. The vagus nerve neural pathways project to the nucleus of the solitary tract (NTS), parabrachial nucleus (PBN), locus coeruleus (LC), the dorsal raphe nucleus (DRN), the caudal ventrolateral medulla (CVLM), and rostral ventrolateral medulla (RVLM). The stimuli generated by the IMD 200 may include a pre-programmed sequence or sweep of electrical pulses applied at different device stimulation parameters. The stimulation parameters may be synchronized with the acquisition and storing of the medical images.

In one embodiment, when the medical images indicate that the targeted regions are activated by stimulation signals provided by the IMD 200, a finer resolution of stimulation parameters may be implemented to further activate more targeted brain regions. Depending on the particular disorder being treated, specific brain areas may be targeted for modulation. These specific brain regions may include, but are not limited to the insula, subcallosal area, cingulated, thalamus, prefrontal cerebral cortex, brain stem, cerebellum, and white matter tracts leading to an aforementioned area, centromedian fascicular complex, ventral medial (Vim) thalamic nucleus, ventral posterior medical nucleus (VPM), parafascicular complex, other portion of the thalamus, subthalamic nucleus (STN), caudate, putamen, cingulate gyrus, paraventricular nucleus of the hypothalamus, the bed nucleus of the stria terminalis, the prefrontal cortex, the supraoptic nucleus, and forebrain circumventricular organs, ventral tegmentum, the substantia nigra pars compacta, ventral medial nucleus (VMb), amygdala, basal ganglia, the sugthalamic nucleus, substantia nigra, pallidal, cerebellum, motor cortex, hypothalamus, substantia innominata, nucleus accumbens, anterior cingulate cortex, the insular cortical region, and/or the area tempestas. Once the aforementioned brain regions are activated, as detected by the imaging equipment, the specific stimulation parameters may be stored in the memory of the IMD 200. These device stimulation parameters or parameter sets may then be utilized for the patient's treatment regimen.

The medical imaging system 250 provides for acquiring medical imaging data, which may refer to an evaluation of an area of a patient's body that is not normally visible. Those skilled in the art having the present disclosure may utilize a variety of types of medical imaging systems in conjunction with embodiments of the present invention and remain within the scope and the spirit of the present invention. Various examples of brain imaging systems are listed below, but they are not intended to be limiting as it would be apparent to those skilled in the art having benefit of the present disclosure that a variety of types of medical imaging may be used in conjunction with the embodiments of the present invention.

Various types of brain imaging system may be utilized herein. For example, the medical imaging system may comprise a computed axial tomography (CT or CAT scan). CAT scans may refer to scanning using a series of x-rays of the head taken from different angles. A computer program may then use a set of equations to estimate the amount of x-rays that was absorbed in a small area within a cross-section of the brain.

Another type of brain scan imaging may include Phototron Emission Tomography (PET). PET refers to measuring emissions from radioactively labeled chemicals that have been injected into the bloodstream. The resulting data is used to produce two-dimensional or three-dimensional images of the distribution of the chemical throughout the brain. A cyclotron produces the phototron emitting radio scopes. The chemicals are labeled with the radioactive matter. The labeled compound, i.e., the radiotracer, is injected into the bloodstream and makes its way to the brain. The sensors relating to the PET scanner then detects the resulting radioactivity as the compound accumulates in different regions of the brain. PET provides for indications of blood flow, oxygen, and glucose metabolism in the tissues of the brain.

Another imaging medical imaging technique is a single photon emission computed tomography (SPECT). SPECT uses gamma ray emitting radioisotopes and a gamma camera to record data. The data is used by a computer to construct two-dimensional and three-dimensional images of active brain regions.

Another imaging technique includes electroencephalography (EEG), which provides for using electrodes placed on the scalp to detect and measure electrical activity emanating from the brain. Yet another medical imaging technique includes magneto encephalography (MEG). MEG is similar to an EEG, but for the fact that magnetic fields are measured instead of electric fields.

Another type of medical imaging technique may include magnetic resonance imaging (MRI). MRI techniques utilize magnetic fields and radio waves to produce two-dimensional or three-dimensional images of brain structures. This imaging data may be acquired without the use of radioactive tracers being injected into the brain. When a magnetic field is imposed upon a subject, each point in space has a unique radio frequency at which the signal is received and transmitted. Various sensors may then read the frequencies and a computer uses the information to correlate and organize the data into an image. Various changes in structures over time may be detected in utilizing MRI data.

There are a variety of types of MRI techniques. For example, a diffusion MRI (Magnetic Resonance Imaging) may be used to perform a brain scan. Diffusion MRI generally relates to measuring the mobility of water molecules in the brain in a non-invasive fashion. As water molecules tend to diffuse along the brain's white-matter fibers, a map relating to the structure and integrity of the major white-matter tracts may be developed in a three-dimensional fashion. Effectively, diffusion MRI provides for a map of the brain's wiring to provide an indication on how various brain regions are interconnected and how certain diseases, such as strokes, intracranial tumors, schizophrenia, etc., affect white matter and cause neurological dysfunction. These dysfunctions may be treated by embodiments of the present invention.

Another type of MRI that may be utilized by embodiments of the present invention is functional MRI. Functional MRI provides for detecting brain activity during execution of behavioral tasks. Functional MRI may provide for indications of the brain's reaction to various disorders, such as psychiatric disorders, language disorders, aging disorders, pain issues, etc. These disorders may be treated utilizing embodiments of the present invention. Functional MRI provides for detecting changes in the concentration of oxygenated blood in the brain, therefore, various disorders may be correlated to certain regions of the brain. Oxygenated blood in the correlated regions may provide indications of the extent of the disorder and/or any stimulation that may be performed to that region.

Another example of an MRI may be a magnetic resonance spectroscopy (MRS). MRS refers to detection of biochemicals, such as metabolites that generate MRI signals. The amount of particular metabolites can be measured if the voxel size is sufficiently large to achieve a minimum amount of signal to noise ratio. Metabolites, such as creatine, choline, M-Acetylaspartate and lactate may be measured, which may indicate several disorders relating to these metabolites. Embodiments of the present invention may treat these disorders. Another type of imaging may refer to structural imaging, which may relate to imaging that measures brain volumes or volumes of sub-regions of the brain.

Structural imaging may also refer to studying diffuse changes in gray matter, white matter and/or to assess localized lesions. Structural imaging studies may include comparing the appearance of a cerebral infarct on different imaging modalities over time and relating these to a patient's clinical features and/or outcome. In other words, various data received by performing structural imaging may be correlated to particular disorders exhibited by the patient. These disorders may include other neurological disorders, which may be treated by utilizing embodiments of the present invention. The various types of medical imaging techniques may be utilized to implement embodiments of the present invention. However, embodiments of the present invention are not limited to utilizing the exemplary medical imaging techniques provided herein.

Figure 3:
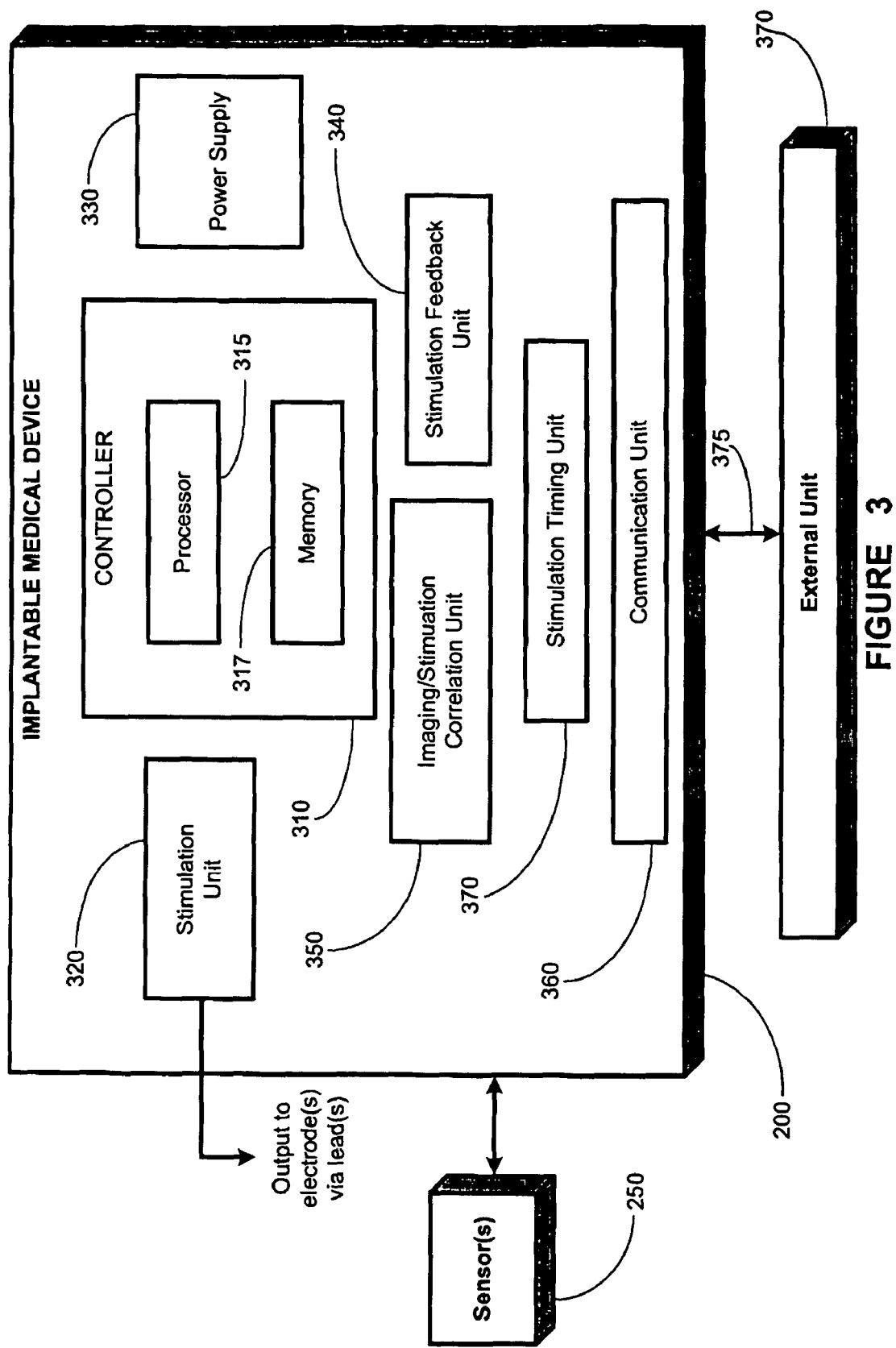
FIG. 3 illustrates a block diagram depiction of the implantable medical device of FIG. 1, in accordance with one illustrative embodiment of the present invention.

Turning now to FIG. 3, a more detailed block diagram depiction of the IMD 200 of FIG. 2, in accordance with one illustrative embodiment of the present invention is provided. The IMD 200 may be used for stimulation to treat various disorders, such as epilepsy, mood disorders, eating disorders, chronic pain disorders, heart rhythm disorders, etc. The IMD 200 may be coupled to various leads, e.g., 122, 134, 137 (FIGS. 1A, 1B, 1D). Stimulation signals used for therapy may be transmitted from the IMD 200 to target areas of the patient's body, specifically to various electrodes associated with the leads 122. Stimulation signals from the IMD 200 may be transmitted via the leads 122 to stimulation electrodes associated with the electrode assembly 125 (FIG. 1A). Further, signals from sensor electrodes, e.g., 133, 136 (FIG. 1B) associated with corresponding leads, e.g., 134, 137, may also traverse the leads back to the IMD 200.

The IMD 200 may comprise a controller 310 capable of controlling various aspects of the operation of the IMD 200. The controller 310 is capable of receiving internal data and/or external data and generating and delivering a stimulation signal to target tissues of the patient's body. For example, the controller 310 may receive manual instructions from an operator externally, or may perform stimulation based on internal calculations and programming. The controller 310 is capable of affecting substantially all functions of the IMD 200.

The controller 310 may comprise various components, such as a processor 315, a memory 317, etc. The processor 315 may comprise one or more micro controllers, microprocessors, etc., that are capable of executing a variety of software components. The memory 317 may comprise various memory portions, where a number of types of data (e.g., internal data, external data instructions, software codes, status data, diagnostic data, etc.) may be stored. The memory 317 may comprise random access memory (RAM) dynamic random access memory (DRAM), electrically erasable programmable read-only memory (EEPROM), flash memory, etc.

The IMD 200 may also comprise a stimulation unit 320. The stimulation unit 320 is capable of generating and delivering a variety of electrical neurostimulation signals to one or more electrodes via leads. The stimulation unit 320 is capable of generating a therapy portion, a ramping-up portion, and a ramping-down portion of the stimulation signal. A number of leads 122, 134, 137 may be coupled to the IMD 200. Therapy may be delivered to the leads 122 by the stimulation unit 320 based upon instructions from the controller 310. The stimulation unit 320 may comprise various types of circuitry, such as stimulation signal generators, impedance control circuitry to control the impedance "seen" by the leads, and other circuitry that receives instructions relating to the type of stimulation to be performed. The stimulation unit 320 is capable of delivering a controlled current stimulation signal to the leads and to the electrodes.

The IMD 200 may also comprise a power supply 330. The power supply 330 may comprise a battery, voltage regulators, capacitors, etc., to provide power for the operation of the IMD 200, including delivering the stimulation signal. The power supply 330 comprises a power-source battery that in some embodiments may be rechargeable. In other embodiments, a non-rechargeable battery may be used. The power supply 330 provides power for the operation of the IMD 200, including electronic operations and the stimulation function. The power supply 330 may comprise a lithium/thionyl chloride cell or a lithium/carbon monofluoride cell. Other battery types known in the art of implantable medical devices may also be used.

The IMD 200 also comprises a communication unit 360 capable of facilitating communications between the IMD 200 and various devices. In particular, the communication unit 360 is capable of providing transmission and reception of electronic signals to and from an external unit 370. The external unit 370 is capable of receiving control signal from the imaging/IMED control unit 280. The imaging/IMD control unit 280 may provide timing data to the IMD 200 via the external device 270 to allow for synchronization of the delivery of stimulation signals with the acquisition of medical imaging data. Further, the external device 370 may provide stimulation control parameter data from the IMD 200 to the imaging/IMD control unit 280 for correlation of medical imaging and stimulation control parameters.

The external unit 370 may be a device that is capable of programming various modules and stimulation parameters of the IMD 200. In one embodiment, the external unit 370 comprises a computer system that is capable of executing a data-acquisition program. The external unit 370 may be controlled by a healthcare provider, such as a physician, at a base station in, for example, a doctor's office. The external unit 370 may be a computer, preferably a handheld computer or PDA, but may alternatively comprise any other device that is capable of electronic communications and programming. The external unit 370 may download various parameters and program software into the IMD 200 for programming the operation of the IMD 200. The external unit 370 may also receive and upload various status conditions and other data from the IMD 200. The communication unit 360 may be hardware, software, firmware, and/or any combination thereof. Communications between the external unit 370 and the communication unit 360 may occur via a wireless or other type of communication, illustrated generally by line 375 in FIG. 3.

The IMD 200 may also comprise an imaging-stimulation correlation unit 350. The correlation unit 350 provides for correlating various imaging data to particular stimulation that was employed by the IMD 200. Imaging data may provide for an indication as to any effects/modulation in the brain that was induced by a stimulation that was delivered by the IMD 200. The correlated data provided by the correlation unit 350 may provide an indication of the effectiveness of the stimulation, including the impact of the stimulation upon a targeted region of the brain.

The IMD 200 may also comprise a stimulation feedback unit 340. The stimulation feedback unit 340 is capable of providing data relating to changes in stimulation parameters based upon an analysis of the correlated imaging and stimulation data. For example, various characteristics of a stimulation signal may be altered based upon the correlated imaging and stimulation data. For example, stimulation parameters, such as pulse width, frequency, amplitude, polarity, etc., may be altered based upon feedback calculations performed using the correlation data. The stimulation feedback unit 340 may also provide data to a stimulation timing unit 370. The stimulation timing unit 370 is capable of determining a timing to synchronize the operation of the medical imaging system 250 and the IMD 200. The stimulation timing unit 370 provides for controlling the timing of the IMD 200 to allow for the synchronization of the operation of the IMD 200 with the medical imaging system based upon data from the imaging/IMD control unit 280 of FIG. 2.

The imaging-stimulation correlation unit 350, stimulation feedback unit 340, and/or the stimulation timing unit 370 may be standalone units that may comprise hardware, software, firmware components, and/or any combination thereof. Alternatively, the imaging-stimulation correlation unit 350, stimulation feedback unit 340, and/or the stimulation timing unit 370 may be integrated into the controller 310.

The IMD 200 is capable of delivering stimulation that can be intermittent, periodic, random, paired-pulses, coded, and/or patterned. The stimulation signals may comprise an electrical stimulation frequency of approximately 0.1 to 2500 Hz. The stimulation signals may comprise a pulse width in the range of approximately 1-2000 microseconds. The stimulation signals may comprise current amplitude in the range of approximately 0.1 mA to 10 mA. Stimulation may be delivered through either the cathode (−) electrode or anode (+) electrode.

Figure 4:
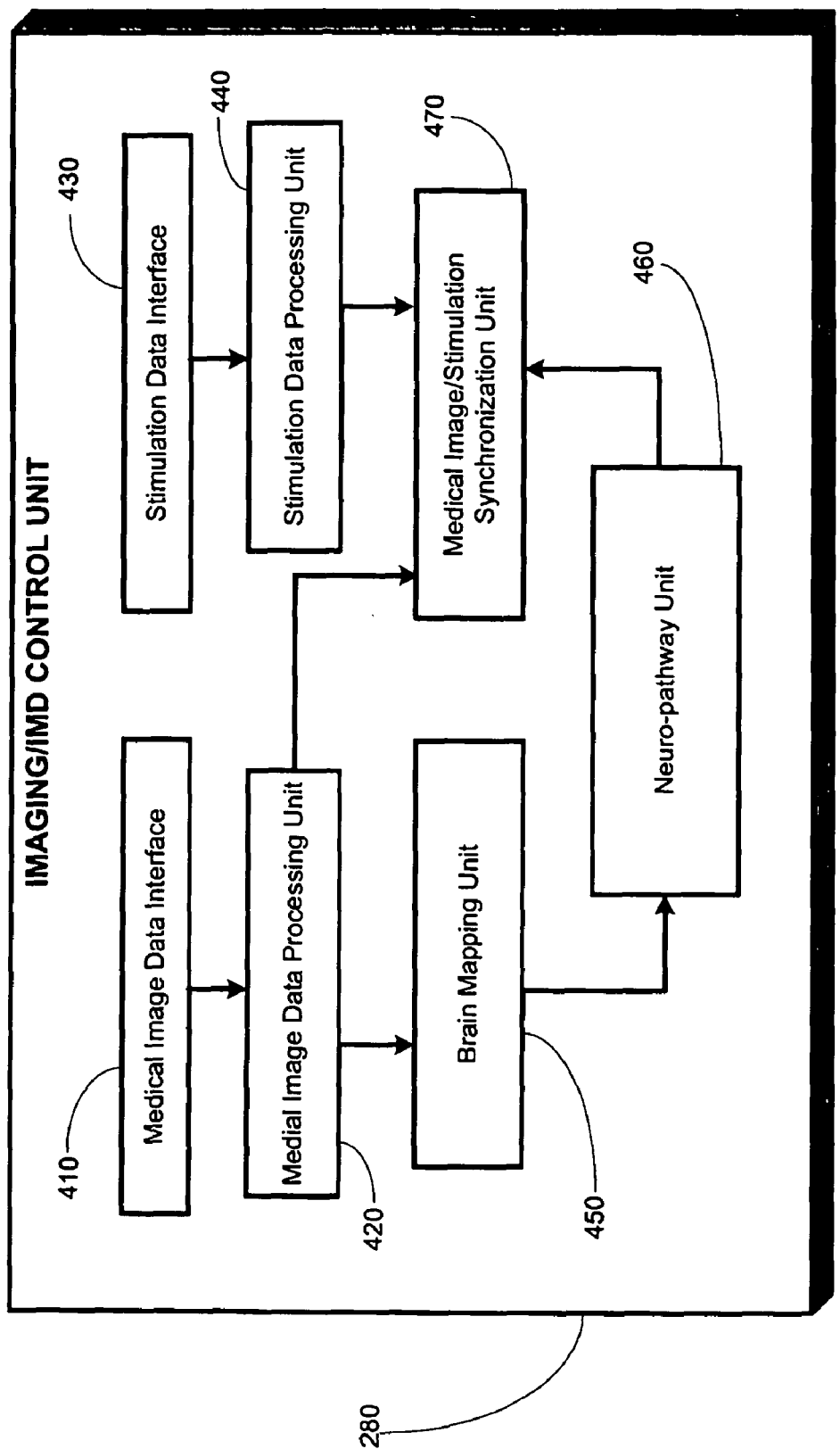
FIG. 4 illustrates a block diagram depiction of an imaging/IMD control unit of FIG. 3, in accordance with one illustrative embodiment of the present invention.

Turning now to FIG. 4, a more detailed block diagram depiction of the imaging/IMD control unit 280 of FIG. 2 is provided. The imaging/IMD control unit 280 may comprise a medical image data interface 410 capable of receiving medical image/brain scan data from the medical imaging system 250 (FIG. 2). The control unit 280 may also comprise a stimulation data interface 430 that is capable of communicating with the IMD 200 via the external device 270. Stimulation data may refer to data relating to various stimulation characteristics, such as pulse width, frequency, amplitude, etc., that was used to perform previous stimulation, as well as to the timing of such stimulation. The stimulation data interface 430 provides stimulation data to a stimulation data processing unit 440. The stimulation data processing unit 440 processes various stimulation data that define the type of stimulation and the timing that was used to deliver this stimulation.

The medical image data interface 410 may provide medical imaging data to a medical image data processing unit 420. The medical image processing unit 420 processes the medical image data. This processing may include analog filter, analog-to-digital conversion, digital filtering, digital signal processing (DSP), buffering, etc. The medical image data processing unit 420 may also receive data relating to the scan of the brain, as well as medical imaging control information.

The control unit 280 may also comprise a brain mapping unit 450. The brain mapping unit 450 is capable of generating various brain maps that may be used to analyze the effectiveness of the stimulation, as well as provide adaptive feedback adjustments for delivering stimulation. The brain mapping unit 450 provides the brain mapping data to a neuro-pathway unit 460. The neuro-pathway unit 460 is capable of performing several tasks that lead to determining a pathway to a targeted section of the brain region utilizing stimulation. In other words, various brain mapping are examined to determine whether the stimulation is effective in reaching or directing the stimulation effect to a target brain region. The brain mapping provides data for navigating stimulation effects/modulation throughout various regions of the brain until the target region of the brain is adequately stimulated.

The neuro-pathway unit 460 is capable of determining which section of the brain to approach using an upcoming stimulation. The neuro-pathway unit 460 may perform a multi-focal stimulation adjustment process or a "safe-cracking" process. The multi-focal stimulation process (i.e., "safe cracking") may refer to a means for iteratively navigating the various neural connections in the brain to access a distal point of interest in the brain. The distal point of interest may be a predetermined region of the brain based upon the type of disorder being treated. The iterative navigation process may include directing stimulation by examining the brain scan mapping from a cranial nerve to the brainstem and on to specific sub-level nuclei (e.g., thalamic nuclei). This navigation provides for detecting the various stimulation effects in the brain by generating the brain mapping. The neural path to the target region of the brain is iteratively navigated by performing a stimulation, determining a brain map signature, and adjusting the stimulation to continue on a neural path until the target region of the brain has been adequately stimulated. The term "navigate" may refer to sequential stimulation and/or for overlap between the sequential stimulations such that a multi-focal stimulation may be performed. The navigation process includes performing an overlapping and/or sequentially navigating or iteratively guiding stimulation effects throughout various regions of the brain until the targeted region of the brain has been stimulated according to a predetermined threshold. The predetermined threshold may include a predetermined level of blood flow to the targeted region, a predetermined level of electrical activity associated with the targeted region, a predetermined level of chemical activity, and/or the like.

Medical imaging data, stimulation data, and data from the neuro-pathway unit 460 may be utilized by a medical image/stimulation synchronization unit 4170 to control the timing of the delivery of stimulation by the IMD 200 and the scanning performed by the medical imaging system 250. Therefore, a controlled timing of stimulation therapy, followed by brain scanning, which in turn may be followed by additional stimulation therapy, may be performed until the effects of the stimulation are navigated through the brain to deliver stimulation effects to the target region. Subsequently, the stimulation parameters may then be set such that subsequent stimulations sufficiently impact the region of the brain that has been targeted. The region of the brain that has been targeted may be based upon a predetermined table that correlates various stimulation effects and brain regions to particular disorders.

Figure 5:
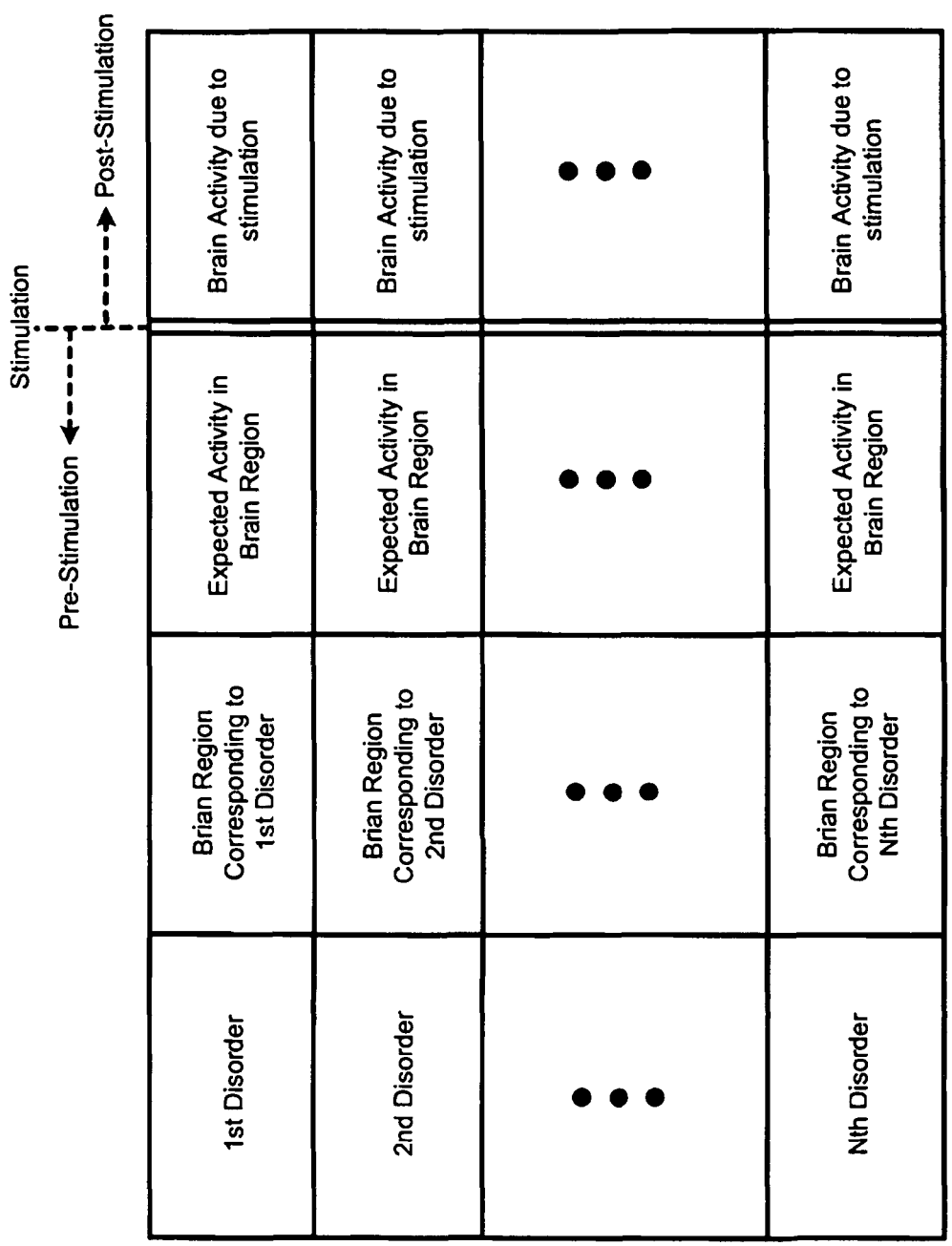
FIG. 5 illustrates a table that associates particular disorders to various brain regions and related expected activity in the brain regions, in accordance with one illustrative embodiment of the present invention.

Turning now to FIG. 5, an exemplary table that may be utilized by the imaging/IMD control unit 280, to target various brain regions is illustrated. The table in FIG. 5 illustrates a tabulation of a first disorder, which may be related to a corresponding brain region that may have been clinically determinative of being related to the disorder. Based upon the severity of the disorder in a patient, an expected activity in the brain region due to the disorder may also be charted in the table of FIG. 5. Therefore, with the information relating to the disorder and its corresponding brain region and the expected brain activity, a brain map may be generated to determine whether a stimulation delivered to a cranial nerve is capable of producing an effect to the desired brain region to treat the disorder.

The table of FIG. 5 may also include a post stimulation section, which may list the activity in the brain region that occurs due to stimulation. For example, if the effects of the stimulation have not adequately been fed to the targeted brain region corresponding to a particular disorder, the activity due to stimulation may simply be the same as the expected activity in the brain region in a pre-stimulation area of the table. Therefore, a determination may be made that if the expected activity and the post-stimulation activity are the same, the stimulation did not achieve an effect to the brain region that is correlated to a particular disorder. Hence, various brain mappings may be performed to compare the expected activity of the brain region in the pre-stimulation to the activity due to stimulation in the post-stimulation section of the table, in order to determine whether adequate effect provided by the stimulation has occurred. Based upon this determination, additional changes to the characteristics of the stimulation provided by the IMD 200 may be performed.

The table in FIG. 5 may also include a list of various disorders, such as a first disorder, second disorder through an $N^{th}$ disorder, along with corresponding brain region effects and expected activity in the region, as well as activity due to a stimulation that occurred in the region. These table entries may be used as a look-up table by the imaging IMD control unit 280, or the IMD 200. Accordingly, an adaptive modification of the stimulation may be performed utilizing the actual data received from the medical imaging system 250 and the table of FIG. 5. Utilizing the table in FIG. 5, the medical imaging system data, and the stimulation data, various brain maps may be generated to determine data relating to an adaptive change that may be made to the stimulation parameters.

Figure 6:
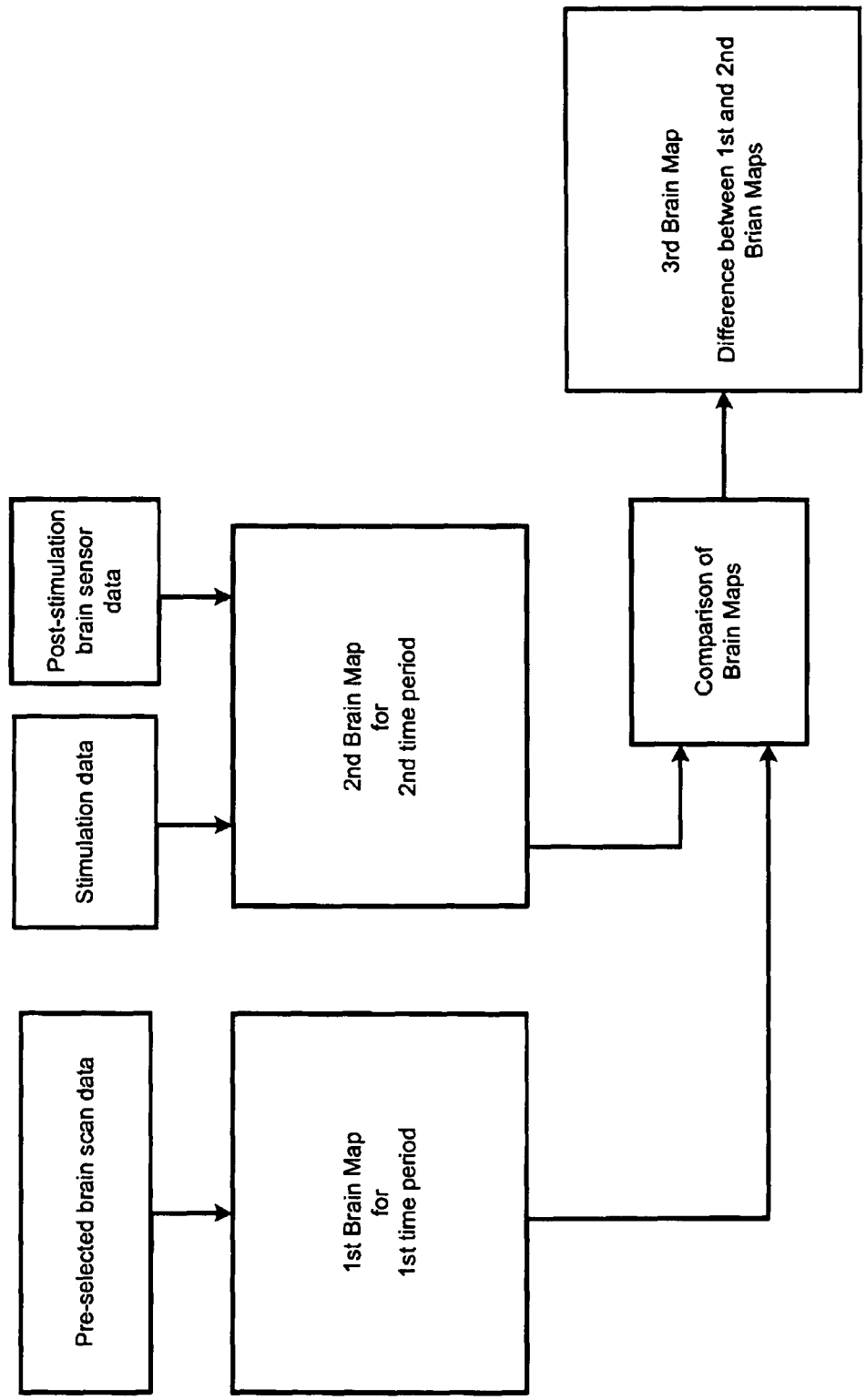
FIG. 6 illustrates a block diagram depiction of the data flow relating to pre-stimulation brain scan data, stimulation data, and a post-stimulation brain scan data, in accordance with one illustrative embodiment of the present invention.

Turning now to FIG. 6, an exemplary data flow of the brain scan stimulation data and the post stimulation brain scan data is illustrated. FIG. 6 illustrates that the pre-stimulation brain scan data acquired by the medical imaging system 250 may be used to provide a first brain map for a first time period in a pre-stimulation environment. In other words, a brain map of a particular patient with a particular disorder may be made in conjunction with the information in the table of FIG. 5. The brain scan relating to a post-stimulation time period may also be acquired by the medical imaging system 250. The post-stimulation brain scan data, as well as the stimulation data, that includes timing of the stimulation as well as other characteristics of the stimulation signal may be used to generate a second brain map for a second time period.

The second brain map is associated with a post-stimulation time period or a time period substantially concurrent to a stimulation. In other words, while a stimulation is being delivered, a brain scan may be performed to generate a brain map that reflects the activity in the brain during stimulation. As described above, the first brain scan provides for measuring brain activity caused by a disorder. In comparison, the second brain map relates to a time period during or after the delivery of stimulation. The brain scan may reflect the region of the brain that is associated with a particular disorder, as provided for by the table illustrated in FIG. 5.

Upon generation of the first and second brain maps, the imaging/IMD control unit 280 may then perform a comparison of the first brain map and the second brain map. This comparison may provide for determining the difference(s) between the first brain map and the second brain map. The difference(s) may be represented by data relating to various values of statistical significance of probability. The comparison of these brain maps may be used to generate a third brain map that reflects the difference between the first and the second brain maps. Accordingly, the third brain map provides the detected differences of a particular region of interest based upon the disorder during a pre-stimulation time period and a post/concurrent stimulation time period. These differences may then be used to determine whether to make changes in the stimulation parameter and the type of changes that are to be made. The type(s) of changes that may be performed include in the stimulation parameter may include, but is not limited to adjusting the controller 310 based on brain imaging data to provide timing of bursts of electrical stimulation to attenuate the neural activity in selective areas of the brain to achieve the desired result. The signal parameters may be adjusted to prompt selective stimulation of the cranial nerves, wherein one or more neural pathways are activated. Neural pathways may include one or more of a pathway of the circuit of Papez, a mesolimbic pathway, a mesocortical pathway, a nigrostriatal pathway, a pathway of the formix, a corticospinal tract pathway, an internal capsule pathway, a corticobulbar tract pathway, a tuberoinfundibular pathway, a corpus callosum pathway, a cerebellorubrothalamocortical pathway, a cerebral peduncular loop, an ascending noradrenergic pathway from the locus coeruleus, an ascending serotonergic pathway from the dorsal raphe, a basal forebrain cholinergic pathway, a brain stem cholinergic pathway, a pathway of the basal limbic system, a pathway of the corticofugal glutamate system, a neurotransmitter pathway from a group consisting of a noradrenergic pathway, a serotonergic pathway, a dopaminergic pathway, a catecholaminergic pathway, a GABAergic pathway, an opioidergic pathway and a cholinergic pathway. Similarly, cranial nerve stimulation may affect neurotransmitter pathways such as noradrenergic, serotoninergic, dopaminergic and cholinergic pathways. Other neural pathways that may be affected include a pathway of the circuit of Papez, a mesolimbic pathway, a mesocortical pathway, a nigrostriatal pathway, a pathway of the formix, a corticospinal tract pathway, an internal capsule, a corticobulbar tract, a tuberoinfundibular pathway, a corpus callosum pathway, a cerebellorubrothalamocortical pathway, a cerebral peduncular loop, an ascending noradrenergic pathway from the locus coeruleus, an ascending serotonergic pathway from the dorsal raphe, a basal forebrain cholinergic pathway, a brain stem cholinergic pathway, a pathway of the basal limbic system, a pathway of the corticofugal glutamate system.

The third brain map may be used to perform an automated adjustment and/or a manual adjustment based from a manual examination of the brain map by a physician. The imaging IMD control unit 280 may then adjust various timing and/or other characteristics of stimulation that may be delivered by the IMD 200. In an alternative embodiment, the adjustment may be performed by the IMD 200 itself using the imaging stimulation correlation unit 350, the stimulation feedback unit 360, and the stimulation timing unit 370.

Figure 7:
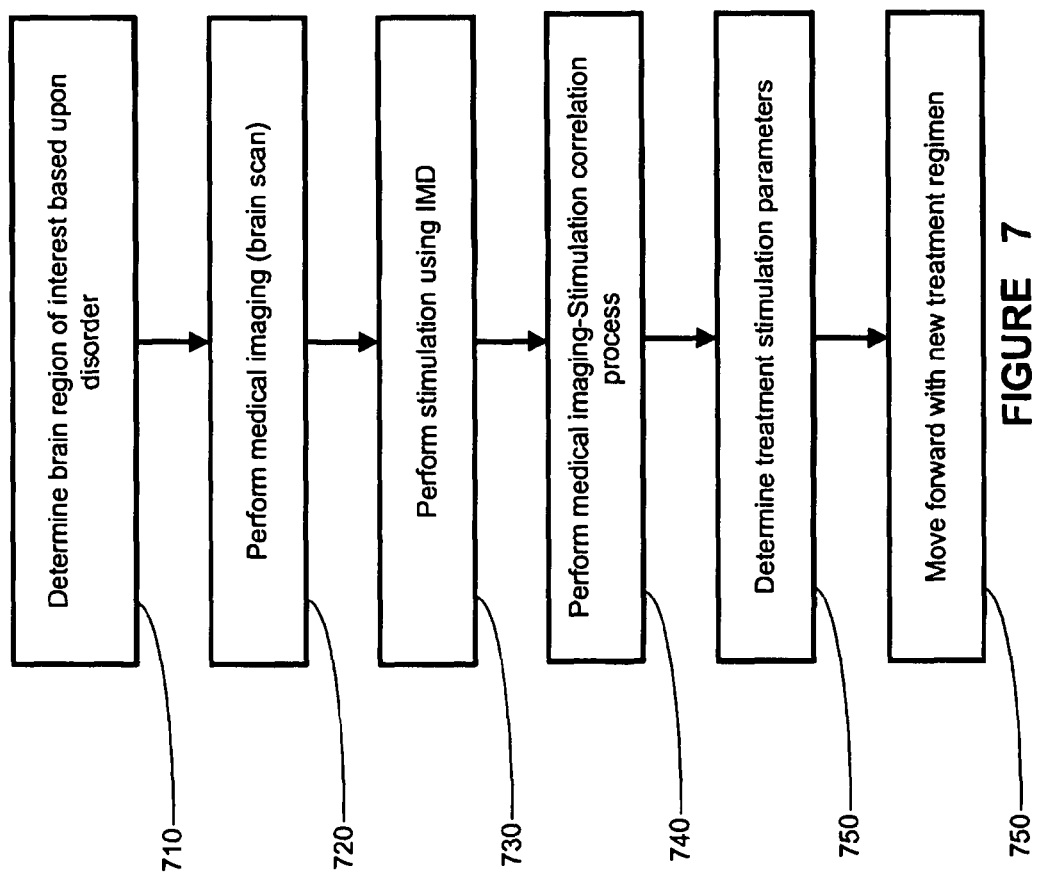
FIG. 7 illustrates a flowchart depiction of the steps of a method for performing an adaptive stimulation, in accordance with one illustrative embodiment of the present invention.

Turning now to FIG. 7, a flowchart depiction of the method of performing an adaptive stimulation process in accordance with an illustrative embodiment of the present invention is provided. The system 200 may be based upon a determination of a brain region of interest, based upon a particular disorder to be treated (block 710). For example, the exemplary table provided in FIG. 5 may provide for a correlation as to the brain region and the sector brain activity of the region based upon a particular disorder being treated. Based upon the region of interest in the brain, a brain scan of the patient may be performed (block 720). As illustrated in FIG. 6, the brain scan data is useful in generating a brain map to examine a pre-stimulation activity of the brain. Based upon the brain scan, a stimulation using the IMD 200 may be performed (block 730). For example, based upon the brain scan, an indication might be revealed as to the type of stimulation to be performed in order to treat a particular disorder. For example, when treating depression in a patient, a target region of the brain may be targeted by stimulating a portion of the cranial nerve, such as the vagus nerve or olfactory nerve.

Upon performing the stimulation, the system 205 may perform a brain scan-stimulation/correlation process (block 740). The brain scan-stimulation/correlation process provides for correlating various data relating to a brain scan resulting from a stimulation process and correlating such data to the stimulation characteristics. A more detailed description of the brain scan-stimulation/correlation process is provided in FIG. 8 and the accompanying description below.

Based upon the brain scan-stimulation/correlation process, the system 205 may determine treatment stimulation parameters for a subsequent stimulation to be delivered to a portion of the patient's body (block 750). In other words, the correlation between the brain scan and the stimulation characteristics may be used to generate an adaptive modification of stimulation parameters to redirect and/or re-emphasize the stimulation effects to the targeted brain region.

Upon performing subsequent stimulation based on the modified stimulation parameter(s), a new treatment regimen of stimulation is followed by the IMD 200 (block 760). This treatment regimen may provide for a more targeted delivery of therapeutic stimulation in order to treat a particular disorder. This may involve more directly affecting the areas of the brain that is believed to be closely associated with a particular disorder. Additionally, the steps described in FIG. 7 may call for various iterative processes of discovering a pathway to the portion of interest in the brain until the area of interest is directly affected by the stimulation provided by the IMD 200.

Figure 8:
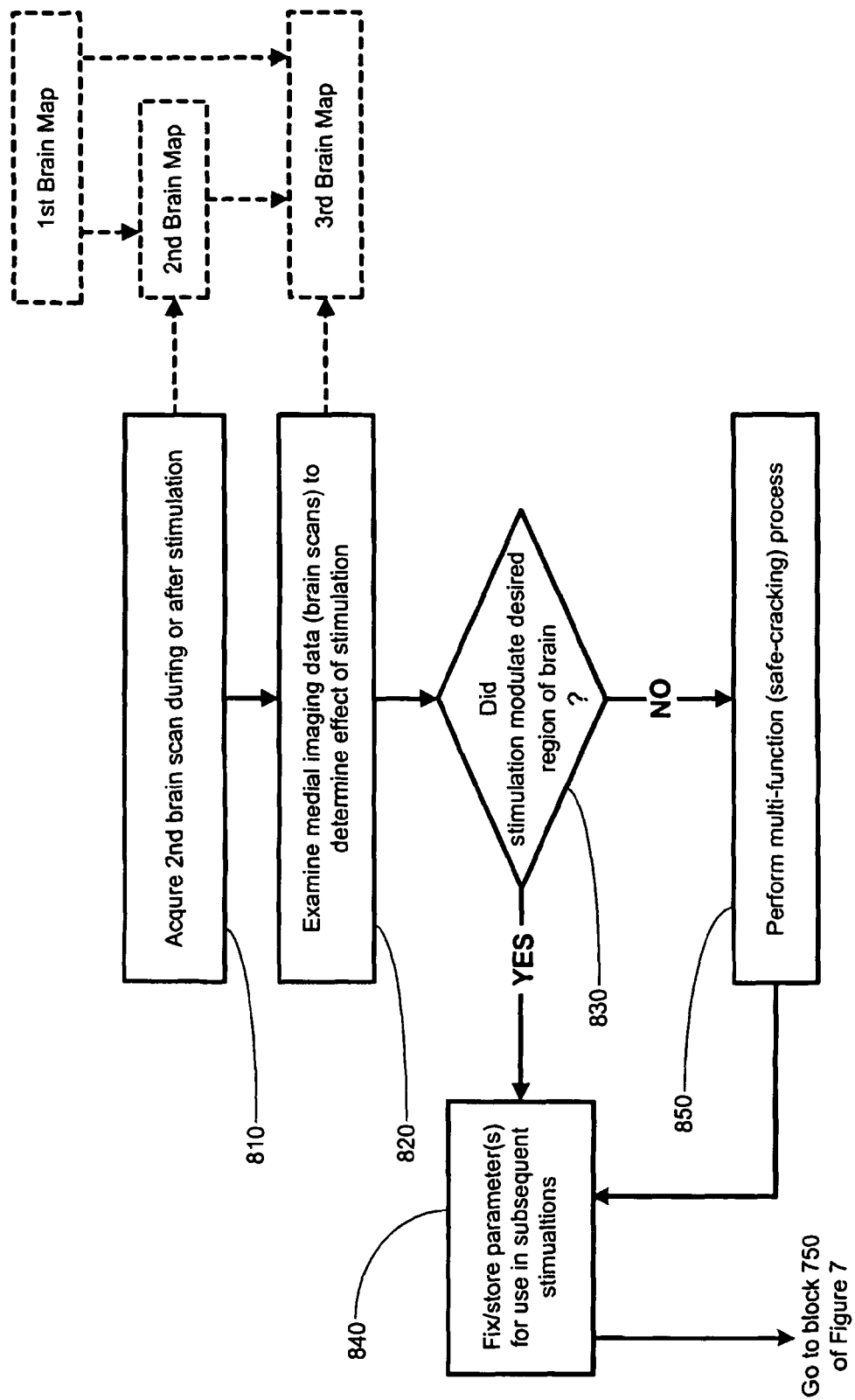
FIG. 8 illustrates a flowchart depiction of the steps for performing a brain scan-stimulation correlation process of FIG. 7, in accordance with one illustrative embodiment of the present invention.

Turning now to FIG. 8, a flowchart depiction of the steps for performing the brain scan stimulation correlation process of block 740 of FIG. 7 is illustrated. The system 205 may acquire subsequent medical imaging data (brain scan data) upon performing a stimulation (block 730 of FIG. 7) during a stimulation or post-stimulation (block 810). As illustrated in FIG. 8, this process may lead to utilizing the post-stimulation brain scan to generate a second brain map. The second brain map illustrates the brain map for a second time period, which may be defined as a post-stimulation or a concurrent-stimulation time period, as illustrated in FIG. 6.

Referring back to FIG. 8, upon performing the brain scan mapping, the IMD 200 may examine the brain scans to determine the effect of the stimulation (block 820). In other words, based upon brain scan data provided by the medical imaging system 250, the IMD 200 may determine whether a targeted area of interest of the brain has been adequately affected by the delivery of the stimulation. This may call for examining and comparing the first brain map and the second brain map, as illustrated in FIG. 6, to generate a third brain map.

Referring back to FIG. 8, based upon the third brain map, i.e., the examination of the brain scans to determine the effect of the stimulation, the IMD 200 may determine whether the immediately preceding stimulation affected/modulated the desired region of the brain, based upon the disorder being treated (block 830). In other words, a determination may be made whether the third brain map showed an appreciable difference between the first brain map and the second brain map. If no appreciable change exists when a comparison of the first brain map and the second brain map is performed, then a determination may be made that the preceding stimulation did not sufficiently alter the characteristics of the region of interest of the brain. However, if a difference is found in the third brain map, based upon a difference between the first and second brain maps, a determination may be made whether significant changes occurred. A determination may then be made that the preceding stimulation indeed caused an appreciable effect in the region of interest of the brain. For example, if a particular region is associated with a first disorder being treated, an increased detection of blood flow, as indicated by the third brain map, in that particular region of interest may be indicative that the most recent stimulation is indeed effective.

Therefore, based upon a determination that the stimulation indeed affects the desired region of the brain, the parameters are fixed/stored for use in subsequent stimulations (block 840). This leads to the block 750 of FIG. 7, which then solidifies the treatment parameters and the trying of the new treatment regimen (block 750-760). Referring back to FIG. 8, upon a determination that the stimulation did not satisfactorily affect the desired region of the brain, a multi-focal stimulation process, i.e., a safecracking process is performed in order to navigate the stimulation effects through the body, to target the region of interest of the brain (block 850). A more detailed description of the type of performing the multi-focal stimulation process of block 850 of FIG. 8 is provided in FIG. 9 and accompanying description below.

Figure 9:
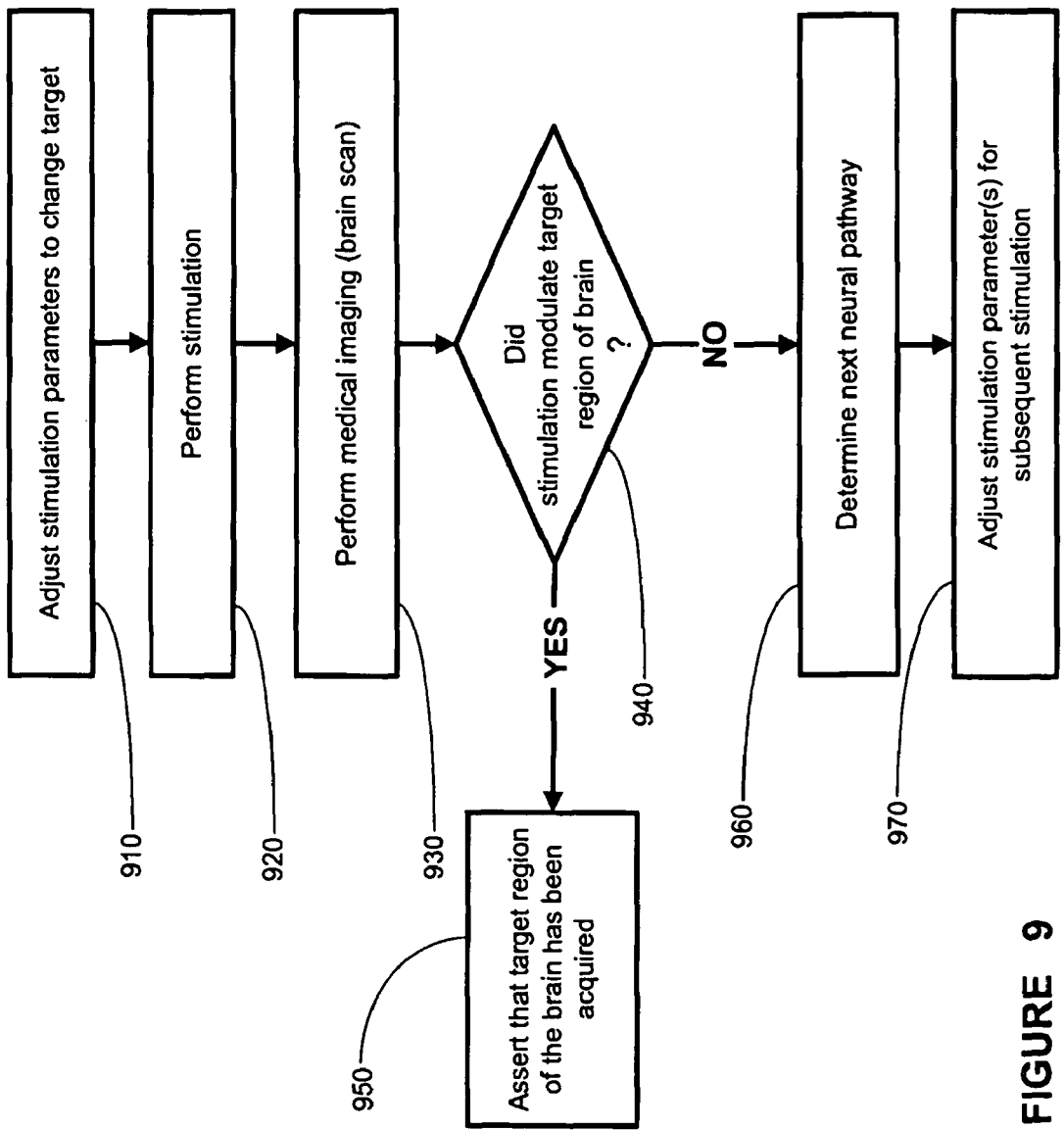
FIG. 9 illustrates a flowchart depiction of the steps relating to a method for performing a multi-focal stimulation process of FIG. 8, in accordance with one illustrative embodiment of the present invention.

Turning now to FIG. 9, a flowchart depiction of the steps for performing the multi-focal stimulation process of FIG. 8 is illustrated. The IMD 200 may adjust stimulation parameter(s) to change the targeting of the stimulation (block 910). This may be based upon the fact that the third brain map indicates that sufficient targeting of a region of interest of the brain has not been achieved by the stimulation provided thus far. Based upon various information, such as information of FIG. 5, and other known physiological facts, a strategy for targeting the next location in order to create a pathway to the region of interest is determined. Based upon this determination, several stimulation parameters may be adjusted and stimulation is then performed based upon these modified parameters (block 920).

Upon performing the stimulation of block 920, a subsequent medical imaging (brain scan) may then be performed (block 930). Therefore, a synchronization between stimulation and scanning of the brain may be coordinated to provide efficient medical imaging (brain scan) data to be correlated with a particular stimulation. Upon performing the medical imaging, the IMD 200 may then determine whether the stimulation affected the targeted brain region (block 940). Upon a determination that the targeted brain region has been sufficiently stimulated, e.g., blood flow to the targeted brain region has satisfactorily increased, an assertion is made that the targeted brain region has been acquired (block 950). Once the target is acquired, the flow of the controller 310 moves to the block 840 of FIG. 8, affixing the parameter for stimulation. A new treatment regimen is then established to perform the targeted stimulation to treat the disorder.

Continuing referring to FIG. 9, upon determination that the stimulation effect did not adequately target the brain region (block 940), a subsequent pathway to navigate through the various brain regions to the targeted regions in the brain is performed (block 960). This may include targeting the energy using a signal with modified amplitude, frequencies, pulse width, etc. Based upon the pathway, the timing signals and the subsequent parameters for performing additional stimulation are sent to the IMD 200 and the stimulation is delivered, as depicted by the loop from block 970 to 920 of FIG. 9. This process may continue until the safecracking process allows for various iterations to target a particular brain region based upon stimulation signals being offered. Utilizing the safecracking process, a sequential adjustment or stimulation delivered in overlapping time periods may be performed to navigate through various regions of the brain to achieve an effect to a particular region that correlates with a particular disorder. Therefore, an adaptive control of the stimulation may be provided.

Therefore, significant delays in adjusting the operation of the IMD 200 may be reduced by the embodiments of the present invention. Embodiments of the present invention provide for automated adaptive analysis, wherein the results may be tabulated into a table. Using this table, an adaptive adjustment of stimulation parameters is made possible by the medical image data and stimulation data analysis provided by the embodiments of the present invention.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. A method for providing an adaptive stimulation using an implantable medical device, comprising:

providing a first stimulation signal comprising a first signal characteristic;

applying said first stimulation signal to an extracranial portion of a cranial nerve for modulation of a target portion of a patient's brain associated with a disorder;

before applying said first stimulation signal, generating a first brain map comprising data relating to states of multiple different portions of the brain, including said target portion of the brain, during a time period prior to application of said first stimulation signal to said cranial nerve, wherein the operation of generating said first brain map comprises acquiring medical imaging data using a medical imaging device selected from the group consisting of a computed axial tomography (CAT) device, a phototron emission tomography (PET) device, a single photon emission computed tomography (SPECT) device, a magneto encephalography (MEG) device, a diffuse optical tomography device (DOT), a functional transcranial doppler device, and a magnetic resonance spectroscopy (MRS) device;

after beginning application of said first stimulation signal, generating a second brain map comprising data relating to states of multiple different portions of the brain, including said target portion of the brain, during a time period after application of said first stimulation signal has begun;

comparing said first brain map to said second brain map to compute a brain-map difference;

generating a third brain map comprising data relating to said brain-map difference, said third brain map indicating whether said target portion of the brain was modulated as a result of said first stimulation signal and whether a non-target portion of the brain was modulated as a result of said first stimulation signal;

determining whether said first stimulation signal sufficiently modulated said target portion of the brain, based at least in part on said third brain map;

modifying said first signal characteristic to generate a second stimulation signal in response to a determination that said target portion of the brain was not sufficiently modulated as a result of said first stimulation signal;

in response to a determination that said target portion of the brain was not sufficiently modulated as a result of said first stimulation signal, determining which region of the brain was affected by said first stimulation signal, based at least in part on said third brain map; and iteratively modifying stimulation signals and computing brain map differences to guide stimulation effects through multiple portions of the brain, until sufficient modulation of said target portion of the brain is detected, to determine stimulation signal characteristics suitable to modulate said target portion of the brain;

wherein said first, second, and third brain maps provide substantially three-dimensional representations.

2. The method of claim 1, wherein applying said first stimulation signal to said portion of said cranial nerve comprises applying said first and said second stimulation signals to a cranial nerve selected from a group consisting of a vagus nerve, a trigeminal nerve, a vestibulocochlear nerve, an olfactory nerve and a glossopharyngeal nerve.

3. The method of claim 1, further comprising synchronizing the timing of the delivery of said first stimulation signal and the timing of acquisition of said medical imaging data.

4. The method of claim 1, wherein acquiring said medical imaging data comprises acquiring at least one of a chemical characteristic, a biological characteristic, and an electrical characteristic associated with a portion of a patient's brain.

5. The method of claim 1, wherein modifying said first signal characteristic comprises modifying at least one of a pulse width, a frequency, a polarity, and an amplitude of said first signal.

6. The method of claim 1, further comprising:

comparing said medical imaging data with an equivalent predetermined reference data to generate a compared value;

correlating said compared value to said first stimulation signal; and modifying said first characteristic based upon said correlating of said compared value to said first stimulation signal.

7. The method of claim 1, wherein determining whether a target portion of the brain has been sufficiently modulated by said first stimulation signal comprises determining whether said target portion of the brain experienced a change in at least one characteristic from the group consisting of a blood flow, a chemical characteristic, an electrical characteristic, and a physical characteristic as a result of said first stimulation signal.

8. The method of claim 1, wherein said target portion of the patient's brain comprises an area from the group consisting of an ascending noradrenergic pathway from the locus coeruleus, an ascending serotonergic pathway from the dorsal raphe, a basal forebrain cholinergic pathway, a brain stem cholinergic pathway, a pathway of the basal limbic system, a pathway of the corticofugal glutamate system, a nigrostriatal pathway, pathway of the circuit of Papez, a mesolimbic pathway, a mesocortical pathway, a corticospinal tract pathway, an internal capsule pathway, a corticobulbar tract pathway, a tuberoinfundibular pathway, a corpus callosum pathway, a pathway of the formix, a cerebellorubrothalamocortical pathway, and a cerebral peduncular loop, a brain stem, a thalamus, an insula, amygdale, hypothalamus, a caudate, a putamen, a cingulate, a subgenual cingulate, a substantia innominata, an anterior cingulate cortex, a substantia nigra, a cingulate gyrus, a prefrontal cerebral cortex, dorsolateral cortex, ventrolateral cortex, a motor cortex, anterior inferior temporal lobes, a subcallosal area, an insular cortical region, a ventral tegmental area, posterior cingulate cortex, dorsal anterior cingulate gyrus, a basal ganglia, a substantia nigra pars compacta, ventral anterior cingulum, dorsal anterior cingulum, a centromedian fascicular complex, an area tempestas, and a bed nucleus of the stria terminalis.

9. The method of claim 1, wherein said medical imaging device is selected from the group consisting of a CAT device, a PET device, and a SPECT device.

10. The method of claim 1, wherein:

said medical imaging device is selected from the group consisting of a CAT device, a PET device, and a SPECT device; and said target portion of the patient's brain comprises an area from the group consisting of an ascending noradrenergic pathway from the locus coeruleus, an ascending serotonergic pathway from the dorsal raphe, a basal forebrain cholinergic pathway, a brain stem cholinergic pathway, a pathway of the basal limbic system, a pathway of the corticofugal glutamate system, a nigrostriatal pathway, pathway of the circuit of Papez, a mesolimbic pathway, a mesocortical pathway, a corticospinal tract pathway, an internal capsule pathway, a corticobulbar tract pathway, a tuberoinfundibular pathway, a corpus callosum pathway, a pathway of the formix, a cerebellorubrothalamocortical pathway, and a cerebral peduncular loop, a brain stem, a thalamus, an insula, amygdale, hypothalamus, a caudate, a putamen, a cingulate, a subgenual cingulate, a substantia innominata, an anterior cingulate cortex, a substantia nigra, a cingulate gyrus, a prefrontal cerebral cortex, dorsolateral cortex, ventrolateral cortex, a motor cortex, anterior inferior temporal lobes, a subcallosal area, an insular cortical region, a ventral tegmental area, posterior cingulate cortex, dorsal anterior cingulate gyrus, a basal ganglia, a substantia nigra pars compacta, ventral anterior cingulum, dorsal anterior cingulum, a centromedian fascicular complex, an area tempestas, and a bed nucleus of the stria terminalis.

\* \* \* \* \*